US009346824B2

(12) United States Patent
Dolente et al.

(10) Patent No.: US 9,346,824 B2
(45) Date of Patent: May 24, 2016

(54) CYCLOHEXYL-4H,6H-5-OXA-2,3,10B-TRIAZA-BENZO[E]AZULENES AS V1A ANTAGONISTS

(71) Applicant: Hoffmann-La Roche Inc., Nutley, NJ (US)

(72) Inventors: Cosimo Dolente, Allschwil (CH); Patrick Schnider, Bottmingen (CH)

(73) Assignee: Hoffman-La Roche, Inc., Little Falls, NJ (US)

( * ) Notice: Subject to any disclaimer, the term of this patent is extended or adjusted under 35 U.S.C. 154(b) by 117 days.

(21) Appl. No.: 14/245,126

(22) Filed: Apr. 4, 2014

(65) Prior Publication Data
US 2014/0221350 A1   Aug. 7, 2014

Related U.S. Application Data

(63) Continuation of application No. PCT/EP2012/069392, filed on Oct. 2, 2012.

(30) Foreign Application Priority Data

Oct. 5, 2011   (EP) ..................................... 11183982

(51) Int. Cl.
A61K 31/553   (2006.01)
C07D 498/04   (2006.01)

(52) U.S. Cl.
CPC .................................... *C07D 498/04* (2013.01)

(58) Field of Classification Search
CPC ........................... A61K 31/553; C07D 498/04
USPC ........................................ 514/211.1; 540/548
See application file for complete search history.

(56) References Cited

FOREIGN PATENT DOCUMENTS

| GB | 2075012 A | 11/1980 |
| WO | 2004/074291 | 9/2004 |
| WO | 2005/068466 | 7/2005 |
| WO | 2005/068472 A1 | 7/2005 |
| WO | 2005/121152 A1 | 12/2005 |

OTHER PUBLICATIONS

Altemus et al., "Abnormalities in the regulation of vasopressin and corticotropin releasing factor section in obsessive-compulsive disorder" Arch Gen Psychiatry 49:9-20 (Jan. 1992).
Aughton et al., "Pharmacological profiling of neuropeptides on rabbit vaginal wall and vaginal artery smooth muscle in vitro" Brit J Pharmacol 155:236-243 ( 2008).
Beal et al., "Preparation of triazolobenzodiazepine derivatives as Vasopressin V1a antagonists" Tetrahedron Letters 52:5913-5917 ( 2011).
Bielsky et al., "Profound impairment in social recognition and reduction in anxiety-like behavior in vasopressin V1a receptor knockout mice" Neuropsychopharmacology 29:483-493 ( 2004).

Brouard et al., "Effect of SR49059, an orally active $V_{1a}$ vasopressin receptor antagonist, in the prevention of dysmenorrhoea" Brit J Obstet Gynaec 107:614-619 ( 2000).
Ebner et al., "Forced swimming triggers vasopressin release within the amygdala to modulate stress-coping strategies in rats" Eur J Neurosci 15:384-388 ( 2002).
Goodman et al., "Pharmacodynamics: Mechanisms of drug action and the relationship between drug concentration and effect" The Pharmacological Basis of Therapeutics 7:35-48 ( 1985).
Gupta et al., "Oxytocin-induced contractions within rat and rabbit ejaculatory tissues are mediated by vasopressin $V_{1A}$ receptors and not oxytocin receptors" Brit J Pharmacol 155:118-126 ( 2008).
Johnson et al., "Discovery of PF-184563, a potent and selective V1a antagonist for the treatment of dysmenorrhoea. The influence of compound flexibility on microsomal stability" Bioorg Med Chem Lett 21:5684-5687 ( 2011).
Kendler et al., "Life event dimensions of loss, humiliation, entrapment, and danger in the prediction of onsets of major depression and generalized anxiety" Arch Gen Psychiatry 60:789-796 (Aug. 2003).
Landgraf et al., "Chronic infusion of a $CRH_1$ receptor antisense oligodeoxynucleotide into the central nucleus of the amygdala reduced anxiety-related behavior in socially defeated rats" Regulatory Peptides 59:229-239 ( 1995).
MacNaught et al., Other Database, (IUPAC ED—Compendium of Chemical Terminology, Blackwell Science, Oxford [U.A.], XP002585006, ISBN: 978-0-86542-684-9), pp. 1 Jan. 1, 1997.
Michelini et al., "Endogenous vasopressin modulates the cardiovascular responses to exercise" Ann NY Acad Sci 897:198-211 ( 1999).

(Continued)

Primary Examiner — Brenda Coleman
(74) Attorney, Agent, or Firm — Mark D. Kafka

(57) ABSTRACT

The present invention provides 4H,6H-5-oxa-2,3,10b-triazabenzo[e]azulenes, which act as V1a receptor modulators, and in particular as V1a receptor antagonists, their manufacture, pharmaceutical compositions containing them and their use as medicaments. The active compounds of the present invention are useful as therapeutics acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

8 Claims, No Drawings

(56) References Cited

OTHER PUBLICATIONS

Neumann, I., "Brain Oxytocin: A key regulator of emotional and social behaviours in both females and males" J Neuroendocrinol 20:858-865 (2008)

Raskind et al., "Antipsychotic drugs and plasma vasopressin in normals and acute schizophrenic patients" Biol Psychiatry 22: 453-462 (1987).

Regier et al., "Prevalence of anxiety disorders and their comorbidity with mood and addictive disorders" Br J Psychiatry Suppl:24-28 (1998).

Robben et al., "Cell biological aspects of the vasopressin type-2 receptor and aquaporin 2 water channel in nephrogenic diabetes insipidus" Am J Physiol Renal Physiol 291:F257-270 (2006).

Thompson et al., "The effects of vasopressin on human facial respones related to social communication" Psychoneuroendocrinology 29:35-48 (2004).

Van Kerckhoven et al., "Chronic vasopressin $V_{1A}$ but not $V_2$ receptor antagonism prevents heart failure in chronically infarcted rats" Eur J Pharmacol 449:135-141 (2002).

Yirmiya et al., "Association between the arginine vasopressin 1a receptor (AVPR1a) gene and autism in a family-based study: mediation by socialization skills" Molec Psych 11:488-494 (2006).

International Search Report and Written Opinion for International Patent Application No. PCT/EP2012/069392, Jul. 11, 2012.

CYCLOHEXYL-4H,6H-5-OXA-2,3,10B-TRIAZA-BENZO[E]AZULENES AS V1A ANTAGONISTS

PRIORITY OF INVENTION

This application is a continuation application and claims priority under 35 U.S.C. 365(c) to International Application No. PCT/EP2012/069392, filed on Oct. 2, 2012, which claims priority EP Application No. 11183982.5 filed on Oct. 5, 2011. The entire content of the applications referenced above are hereby incorporated by reference herein.

FIELD OF INVENTION

The present invention provides 4H,6H-5-oxa-2,3,10b-triaza-benzo[e]azulenes, which act as V1a receptor modulators, and in particular as V1a receptor antagonists, their manufacture, pharmaceutical compositions containing them and their use as medicaments. The present compounds are useful as therapeutics acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

Vasopressin is a 9 amino acid peptide mainly produced by the paraventricular nucleus of the hypothalamus. In the periphery vasopressin acts as a neurohormone and stimulates vasoconstriction, glycogenolysis and antidiuresis.

Three vasopressin receptors, all belonging to the class I G-protein coupled receptors, are known. The V1a receptor is expressed in the brain, liver, vascular smooth muscle, lung, uterus and testis, the V1b or V3 receptor is expressed in the brain and pituitary gland, the V2 receptor is expressed in the kidney where it regulates water reabsorption and mediates the antidiuretic effects of vasopressin (Robben et al.[1]). Compounds with activity at the V2 receptor may therefore cause side-effects on blood homeostasis.

The oxytocin receptor is related to the Vasopressin receptor family and mediates the effects of the neurohormone oxytocin in the brain and the periphery. Oxytocin is believed to have central anxiolytic effects (Neumann[2]). Central oxytocin receptor antagonism might therefore lead to anxiogenic effects, which are regarded as undesired side-effects In the brain vasopressin acts as a neuromodulator and is elevated in the amygdala during stress (Ebner et al.[3]). It is known that stressful life events can trigger major depression and anxiety (Kendler et al.[4]) and that both have very high comorbidity, with anxiety often preceding major depression (Regier et al.[5]). The V1a receptor is extensively expressed in the brain and particularly in limbic areas like the amygdala, lateral septum and hippocampus which are playing an important role in the regulation of anxiety. Indeed V1a knock-out mice show a reduction in anxious behavior in the plus-maze, open field and light-dark box (Bielsky et al.[6]). The downregulation of the V1a receptor using antisense oligonucleotide injection in the septum also causes a reduction in anxious behavior (Landgraf et al.[7]). Vasopressin or the V1a receptor are also implicated in other neuropsychological disorders: genetic studies recently linked sequence polymorphism in the promoter of the human V1a receptor to autistic spectrum disorders (Yirmiya et al.)[8], intranasal administration of vasopressin was shown to influence aggression in human males (Thompson et al.[9]) and vasopressin levels were found to be elevated in schizophrenic patients (Raskind et al.[10]) and patients with obsessive-compulsive disorder (Altemus et al.[11]).

The V1a receptor is also mediating the cardiovascular effects of vasopressin in the brain by centrally regulating blood pressure and heart rate in the solitary tract nucleus (Michelini et al.[12]). In the periphery it induces the contraction of vascular smooth muscles and chronic inhibition of the V1a receptor improves hemodynamic parameters in myocardial infarcted rats (Van Kerckhoven, et al.[13]). Hence, V1a antagonists with improved penetration through the blood-brain barrier are expected to be of advantage.

A vasopressin V1a receptor antagonist was shown to be effective in reducing dysmenorrhea in the clinic (Brouard, et al.[14]). V1a receptor antagonism has also been implicated in the treatment of female sexual dysfunction (Aughton, et al.[15]). In a recent study V1a receptor antagonists were suggested to have a therapeutic role in both erectile dysfunction and premature ejaculation (Gupta, et al.[16]).

SUMMARY OF INVENTION

The present invention provides a compounds of formula I,

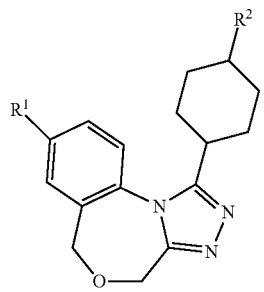

wherein $R^1$ is halogen, and $R^2$ is selected from the group consisting of heteroaryl, unsubstituted or substituted by 1 to 3 substituents individually selected from the group consisting of OH, halogen, cyano, $C_{1-6}$-alkoxy, halogen-C halogen-$C_{1-6}$-alkoxy, $C_{1-6}$ alkoxy $C_{1-6}$ alkyl and hydroxy-$C_{1-6}$-alkyl; i) aryl, unsubstituted or substituted by 1 to 3 substituents individually selected from the group consisting of OH, halogen, cyano, $C_{1-6}$-alkyl, $C_{1-6}$-alkoxy, halogen-$C_{1-6}$-alkyl, halogen-$C_{1-6}$-alkoxy, $C_{1-6}$-alkoxy-$C_{1-6}$-alkyl and hydroxy-$C_{1-6}$-alkyl; ii) $C_{3-7}$-cycloalkyl, unsubstituted or substituted by 1 to 3 substituents individually selected from the group consisting of OH, halogen, cyano, $C_{1-6}$ alkyl, $C_{1-6}$-alkoxy, halogen $C_{1-6}$ alkyl, halogen-$C_{1-6}$-alkoxy, $C_{1-6}$-alkoxy-$C_{1-6}$-alkyl and hydroxy-$C_{1-6}$-alkyl; and iii) $C_{1-6}$-alkyl, unsubstituted or substituted by 1 to 3 substituents individually selected from the group consisting of OH, halogen, cyano, $C_{3-7}$-cycloalkyl, $C_{1-6}$-alkoxy and halogen-$C_{1-6}$-alkoxy; or pharmaceutically acceptable salts thereof.

In another aspect, the present invention provides for compounds that are V1a receptor antagonists, useful for the treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

DETAILED DESCRIPTION OF THE INVENTION

The present invention provides a compound of formula I and their pharmaceutically acceptable salts thereof, the preparation of the above mentioned compounds, medicaments containing them and their manufacture as well as the use of the above mentioned compounds in the therapeutic and/or prophylactic treatment of diseases and disorders which are associated with modulation of the V1a receptor, and in particular with V1a receptor antagonism. A further object of the invention is to provide selective inhibitors of the V1a receptor, since selectivity for the V1a receptor is expected to afford a low potential to cause unwanted off-target related side effects such as discussed above.

Present compounds are useful as therapeutics acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior. Particular indications with regard to the present invention are the treatment of anxiety, depressive disorders, obsessive compulsive disorder, autistic spectrum disorders, schizophrenia, and aggressive behavior.

The following definitions of the general terms used in the present description apply irrespectively of whether the terms in question appear alone or in combination with other groups.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, (isobutyl), 2-butyl (sec-butyl), t-butyl (tert-butyl), isopentyl, 2-ethyl-propyl, 1,2-dimethyl-propyl and the like. Particular "$C_{1-6}$-alkyl" groups have 1 to 4 carbon atoms. Specific groups are methyl and isobutyl.

The term "halogen-$C_{1-6}$-alkyl", alone or in combination with other groups, refers to $C_{1-6}$-alkyl as defined herein, which is substituted by one or multiple halogen, in particular 1-5 halogen, more particular 1-3 halogen ("halogen-$C_{1-3}$-alkyl"), specific groups have 1 halogen or 3 halogens. Particular halogen is fluoro. A particular "halogen-$C_{1-6}$-alkyl" group is fluoro-$C_{1-6}$-alkyl.

The term "hydroxy-$C_{1-6}$-alkyl", alone or in combination with other groups, refers to $C_{1-6}$-alkyl as defined herein, which is substituted by one or multiple —OH, in particular 1-2 —OH, more particular 1 —OH.

The term "$C_{3-7}$-cycloalkyl-$C_{1-6}$-alkyl", alone or in combination with other groups, refers to $C_{1-6}$-alkyl as defined herein, which is substituted by one or multiple $C_{3-6}$-cycloalkyl as defined herein, in particular 1 $C_{3-6}$-cycloalkyl.

The term "$C_{1-6}$-alkoxy-$C_{1-6}$-alkyl", alone or in combination with other groups, refers to $C_{1-6}$-alkyl as defined herein, which is substituted by one or multiple $C_{1-6}$-alkoxy as defined herein, in particular 1-2 $C_{1-6}$-alkoxy, more particular 1 $C_{1-6}$-alkoxy.

The term "cyano", alone or in combination with other groups, refers to N≡C—(NC—).

The term "hydroxy", alone or in combination with other groups, refers to —OH.

The term "halogen", alone or in combination with other groups, denotes chloro (Cl), iodo (I), fluoro (F) and bromo (Br). Particular "halogen" is Cl and F. Specific is Cl.

The term "aryl", alone or in combination with other groups, refers to an aromatic carbocyclic group containing 6 to 14, in particular 6 to 10, carbon atoms and having at least one aromatic ring or multiple condensed rings in which at least one ring is aromatic. Examples of "aryl" include benzyl, biphenyl, indanyl, naphthyl, phenyl (Ph) and the like. Particular "aryl" is phenyl. The term "optionally substituted aryl", alone or in combination with other groups, refers to aryl as defined herein unsubstituted or substituted by 1 to 3 substituents individually selected from the group consisting of OH, halogen, cyano, $C_{1-6}$-alkyl, $C_{1-6}$-alkoxy, halogen-$C_{1-6}$-alkyl, halogen-$C_{1-6}$-alkoxy, $C_{1-6}$-alkoxy-$C_{1-6}$-alkyl and hydroxy-$C_{1-6}$-alkyl.

The term "heteroaryl", alone or in combination with other groups, refers to an aromatic carbocyclic group of having a single 4 to 8 membered ring or multiple condensed rings containing 6 to 14, in particular 6 to 10 ring atoms and containing 1, 2 or 3 heteroatoms individually selected from N, O and S, in particular N and O, in which group at least one heterocyclic ring is aromatic. Examples of "heteroaryl" include benzofuryl, benzoimidazolyl, 1H-benzoimidazolyl, benzooxazinyl, benzoxazolyl, benzothiazinyl, benzothiazolyl, benzothieuyl, benzotriazolyl, furyl, imidazolyl, indazolyl, 1H indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl, pyrrolyl, quinolinyl, tetrazolyl, thiazolyl, thienyl, triazolyl, 6,7-dihydro-5H-[1]pyrindinyl and the like. Particular "heteroaryl" are pyridinyl, benzo[d]isothiazolyl, [1,2,4]oxadiazolyl, isoxazolyl, 4,5,6,7-tetrahydro-benzo[c]isoxazolyl, 4-benzo[d]isoxazolyl and 4,5,6,7-tetrahydro-1H-indazolyl. Specific "heteroaryl" are pyridin-2-yl, 4-benzo[d]isothiazol-3-yl, [1,2,4]oxadiazol-3-yl, isoxazol-3-yl, 4,5,6,7-tetrahydro-benzo[c]isoxazol-3-yl, 4-benzo[d]isoxazol-3-yl and 4,5,6,7-tetrahydro-1H-indazol-3-yl. The term "optionally substituted heteroaryl", alone or in combination with other groups, refers to heteroaryl as defined herein unsubstituted or substituted by 1 to 3 substituents individually selected from the group consisting of OH, halogen, cyano, $C_{1-6}$-alkyl, $C_{1-6}$-alkoxy, halogen-$C_{1-6}$-alkyl, halogen-$C_{1-6}$-alkoxy, $C_{1-6}$-alkoxy-$C_{1-6}$-alkyl and hydroxy-$C_{1-6}$-alkyl.

The term "$C_{1-6}$-alkoxy", alone or in combination with other groups, stands for an —O—$C_{1-6}$-alkyl radical which may be linear or branched, with single or multiple branching, wherein the alkyl group in general comprises 1 to 6 carbon atoms, for example, methoxy (OMe, MeO), ethoxy (OEt), propoxy, isopropoxy (i-propoxy), n-butoxy, i-butoxy (isobutoxy), 2-butoxy (sec-butoxy), t-butoxy (tert-butoxy), isopentyloxy (i-pentyloxy) and the like. Particular "$C_{1-6}$-alkoxy" are groups with 1 to 4 carbon atoms.

The term "halogen-$C_{1-6}$-alkoxy", alone or in combination with other groups, refers to $C_{1-6}$-alkoxy as defined herein, which is substituted by one or multiple halogens, in particular fluoro. Particular "halogen-$C_{1-6}$-alkoxy" is fluoro-$C_{1-6}$-alkoxy.

The term "$C_{3-7}$-cycloalkyl" denotes a monovalent saturated monocyclic or bicyclic hydrocarbon group of 3 to 6 ring carbon atoms. Bicyclic means consisting of two saturated carbocycles having one or more carbon atoms in common. Particular $C_{3-6}$-cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl. A specific example is cyclopentyl.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, sulphuric acid, tartaric acid, trifluoroacetic acid and the like. Particular are formic acid, trifluoroacetic acid and hydrochloric acid. Particular are hydrochloric acid, trifluoroacetic acid and fumaric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. In particular, it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

The term "antagonist" denotes a compound that diminishes or prevents the action of another compound as defined e.g. in Goodman and Gilman's "The Pharmacological Basis of Therapeutics, 7th ed." in page 35, Macmillan Publ. Company, Canada, 1985[17]. In particular, antagonists refers to a compound that attenuates the effect of an agonist. A "competitive antagonist" binds to the same site of a receptor as the agonist but does not activate the receptor, thus blocks the agonist's action. A "non-competitive antagonist" binds to an allosteric (non-agonist) site on the receptor to prevent activation of the receptor. A "reversible antagonist" binds non-covalently to the receptor, therefore can be "washed out". An "irreversible antagonist" binds covalently to the receptor and cannot be displaced by either competing ligands or washing.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as in particular, more particular and most particular definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC[18].

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

In detail, the present invention provides compounds of the general formula I

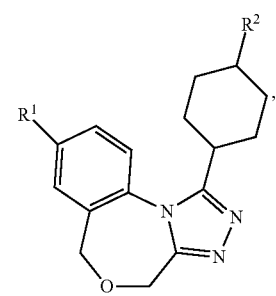

I wherein
R¹ is halogen, and
R² is selected from the group consisting of
  i) heteroaryl, unsubstituted or substituted by 1 to 3 substituents individually selected from the group consisting of OH, halogen, cyano, $C_{1-6}$-alkyl, $C_{1-6}$-alkoxy, halogen-$C_{1-6}$-alkyl, halogen-$C_{1-6}$-alkoxy, $C_{1-6}$-alkoxy-$C_{1-6}$-alkyl and hydroxy-$C_{1-6}$-alkyl;
  ii) aryl, unsubstituted or substituted by 1 to 3 substituents individually selected from the group consisting of OH, halogen, cyano, $C_{1-6}$-alkyl, $C_{1-6}$-alkoxy, halogen-$C_{1-6}$-alkyl, halogen-$C_{1-6}$-alkoxy, $C_{1-6}$-alkoxy-$C_{1-6}$-alkyl and hydroxy-$C_{1-6}$-alkyl;
  iii) $C_{3-7}$-cycloalkyl, unsubstituted or substituted by 1 to 3 substituents individually selected from the group consisting of OH, halogen, cyano, $C_{1-6}$-alkyl, $C_{1-6}$-alkoxy, halogen-$C_{1-6}$-alkyl, halogen-$C_{1-6}$-alkoxy, $C_{1-6}$-alkoxy-$C_{1-6}$-alkyl and hydroxy-$C_{1-6}$-alkyl; and
  iv) unsubstituted or substituted by 1 to 3 substituents individually selected from the group consisting of OH, halogen, cyano, $C_{3-7}$-cycloalkyl, $C_{1-6}$-alkoxy and halogen-$C_{1-6}$-alkoxy;
or pharmaceutically acceptable salts thereof.

A certain embodiment of the present invention provides compounds of the general formula I'

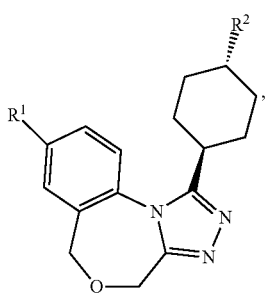

I' wherein
R¹ is halogen, and
R² is selected from the group consisting of
  i) heteroaryl, unsubstituted or substituted by 1 to 3 substituents individually selected from the group consisting of OH, halogen, cyano, $C_{1-6}$-alkyl, $C_{1-6}$-alkoxy, halogen-$C_1$-6-alkyl, halogen-$C_{1-6}$-alkoxy, $C_{1-6}$-alkoxy-$C_{1-6}$-alkyl and hydroxy-$C_{1-6}$-alkyl;
  ii) aryl, unsubstituted or substituted by 1 to 3 substituents individually selected from the group consisting of OH, halogen, cyano, $C_{1-6}$-alkyl, $C_{1-6}$-alkoxy, halogen-$C_{1-6}$-alkyl, halogen-$C_{1-6}$-alkoxy, $C_{1-6}$-alkoxy-$C_{1-6}$-alkyl and hydroxy-$C_{1-6}$-alkyl;
  iii) $C_{3-7}$-cycloalkyl, unsubstituted or substituted by 1 to 3 substituents individually selected from the group consisting of OH, halogen, cyano, $C_{1-6}$-alkyl, $C_{1-6}$-alkoxy, halogen-$C_{1-6}$-alkyl, halogen-$C_{1-6}$-alkoxy, $C_{1-6}$-alkoxy-$C_{1-6}$-alkyl and hydroxy-$C_{1-6}$-alkyl; and
  iv) $C_{1-6}$-alkyl, unsubstituted or substituted by 1 to 3 substituents individually selected from the group consisting of OH, halogen, cyano, $C_{3-7}$-cycloalkyl, $C_{1-6}$-alkoxy and halogen-$C_{1-6}$-alkoxy;
or pharmaceutically acceptable salts thereof.

A certain embodiment of the invention provides a compound as defined herein, wherein R¹ is chloro.

A certain embodiment of the invention provides a compound as defined herein, wherein R² is selected from the group consisting of unsubstituted heteroaryl, heteroaryl substituted by halogen or $C_{1-6}$-alkyl, unsubstituted $C_{1-6}$-alkyl and $C_{1-6}$-alkyl substituted by halogen and $C_{3-7}$-cycloalkyl.

A certain embodiment of the invention provides a compound as defined herein, wherein R² is unsubstituted heteroaryl.

A certain embodiment of the invention provides a compound as defined herein, wherein R² is 4-benzo[d]isothiazolyl.

A certain embodiment of the invention provides a compound as defined herein, wherein R² is 4,5,6,7-tetrahydrobenzo[c]isoxazolyl.

A certain embodiment of the invention provides a compound as defined herein, wherein R² is 4,5,6,7-tetrahydro-1H-indazolyl.

A certain embodiment of the invention provides a compound as defined herein, wherein R² is 4-benzo[d]isoxazol-3-yl.

A certain embodiment of the invention provides a compound as defined herein, wherein R² is heteroaryl substituted by halogen.

A certain embodiment of the invention provides a compound as defined herein, wherein R² is 3-fluoro-pyridinyl.

A certain embodiment of the invention provides a compound as defined herein, wherein R² is heteroaryl substituted by $C_{1-6}$-alkyl.

A certain embodiment of the invention provides a compound as defined herein, wherein R² is 5-methyl-isoxazolyl.

A certain embodiment of the invention provides a compound as defined herein, wherein R² is 5-methyl-[1,2,4]oxadiazolyl.

A certain embodiment of the invention provides a compound as defined herein, wherein R² is unsubstituted $C_{1-6}$-alkyl.

A certain embodiment of the invention provides a compound as defined herein, wherein R² is isobutyl.

A certain embodiment of the invention provides a compound as defined herein, wherein R² is $C_{1-6}$-alkyl substituted by halogen and $C_{3-7}$-cycloalkyl.

A certain embodiment of the invention provides a compound as defined herein, wherein R² is cyclopentyl-difluoromethyl.

A certain embodiment of the invention provides a compound as defined herein, wherein R² is selected from the group consisting of 3-fluoro-pyridinyl, 4-benzo[d]isothiazolyl, 5-methyl-[1,2,4]oxadiazolyl, 5-methyl-isoxazolyl, 4,5, 6,7-tetrahydro-benzo[c]isoxazolyl, 4,5,6,7-tetrahydro-1H-indazolyl, isobutyl, cyclopentyl-difluoro-methyl and 4-benzo[d]isoxazolyl.

A certain embodiment of the invention provides a compound as defined herein, selected from the group consisting of
8-Chloro-1-[4-(3-fluoro-pyridin-2-yl)-cyclohexyl]-4H,6H-5-oxa-2,3,10b-triaza-benzo[e]azulene,
1-(4-Benzo[d]isothiazol-3-yl-cyclohexyl)-8-chloro-4H,6H-5-oxa-2,3,10b-triaza-benzo[e]azulene,
8-Chloro-1-[4-(5-methyl-[1,2,4]oxadiazol-3-yl)-cyclohexyl]-4H,6H-5-oxa-2,3,10b-triaza-benzo[e]azulene,
8-Chloro-1-[4-(5-methyl-isoxazol-3-yl)-cyclohexyl]-4H,6H-5-oxa-2,3,10b-triaza-benzo[e]azulene,
8-Chloro-1-[4-(4,5,6,7-tetrahydro-benzo[c]isoxazol-3-yl)-cyclohexyl]-4H,6H-5-oxa-2,3,10b-triaza-benzo[e]azulene,
8-Chloro-1-[4-(4,5,6,7-tetrahydro-1H-indazol-3-yl)-cyclohexyl]-4H,6H-5-oxa-2,3,10b-triaza-benzo[e]azulene,
8-Chloro-1-(4-isobutyl-cyclohexyl)-4H,6H-5-oxa-2,3,10b-triaza-benzo[e]azulene,
8-Chloro-1-[4-(cyclopentyl-difluoro-methyl)-cyclohexyl]-4H,6H-5-oxa-2,3,10b-triaza-benzo[e]azulene, and
1-(4-Benzo[d]isoxazol-3-yl-cyclohexyl)-8-chloro-4H,6H-5-oxa-2,3,10b-triaza-benzo[e]azulene
or pharmaceutically acceptable salts thereof.

A certain embodiment of the invention provides a compound as defined herein, which is 8-Chloro-1-[4-(3-fluoro-pyridin-2-yl)-cyclohexyl]-4H,6H-5-oxa-2,3,10b-triaza-benzo[e]azulene.

A certain embodiment of the invention provides a compound as defined herein, which is 1-(4-Benzo[d]isothiazol-3-yl-cyclohexyl)-8-chloro-4H,6H-5-oxa-2,3,10b-triaza-benzo[e]azulene.

A certain embodiment of the invention provides a compound as defined herein, which is 8-Chloro-1-[4-(5-methyl-[1,2,4]oxadiazol-3-yl)-cyclohexyl]-4H,6H-5-oxa-2,3,10b-triaza-benzo[e]azulene.

A certain embodiment of the invention provides a compound as defined herein, which is 8-Chloro-1-[4-(5-methyl-isoxazol-3-yl)-cyclohexyl]-4H,6H-5-oxa-2,3,10b-triaza-benzo[e]azulene.

A certain embodiment of the invention provides a compound as defined herein, which is 8-Chloro-1-[4-(4,5,6,7-tetrahydro-benzo[c]isoxazol-3-yl)-cyclohexyl]-4H,6H-5-oxa-2,3,10b-triaza-benzo[e]azulene.

8-Chloro-1-[4-(4,5,6,7-tetrahydro-1H-indazol-3-yl)-cyclohexyl]-4H,6H-5-oxa-2,3,10b-triaza-benzo[e]azulene.

A certain embodiment of the invention provides a compound as defined herein, which is 8-Chloro-1-(4-isobutyl-cyclohexyl)-4H,6H-5-oxa-2,3,10b-triaza-benzo[e]azulene.

A certain embodiment of the invention provides a compound as defined herein, which is 8-Chloro-1-[4-(cyclopentyl-difluoro-methyl)-cyclohexyl]-4H,6H-5-oxa-2,3,10b-triaza-benzo[e]azulene.

A certain embodiment of the invention provides a compound as defined herein, which is 1-(4-Benzo[d]isoxazol-3-yl-cyclohexyl)-8-chloro-4H,6H-5-oxa-2,3,10b-triaza-benzo[e]azulene.

One embodiment of the invention is a process for synthesis a compound of formula I as described herein, which process comprises reacting a compound of formula II with a compound of formula III to a compound of formula I

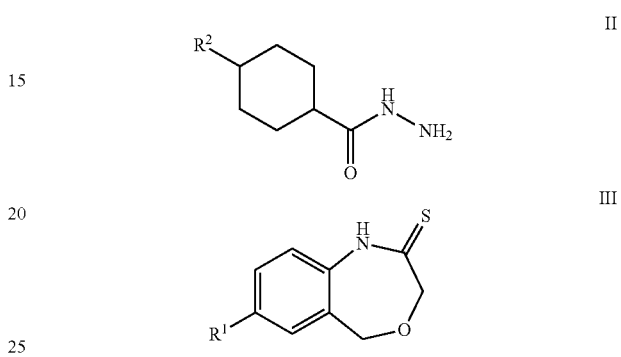

wherein $R^1$ and $R^2$ are as defined herein.

One embodiment of the invention is a compound of formula I, whenever prepared by a process as defined herein.

One embodiment of the invention is a compound of formula I for use as therapeutically active substance.

One embodiment of the invention is a compound of formula I for the use as therapeutically active substance for the therapeutic and/or prophylactic treatment of diseases and disorders which are associated with Via receptor antagonism.

One embodiment of the invention is a compound of formula I for the use as therapeutically active substance acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

One embodiment of the invention is a pharmaceutical composition comprising a compound of formula I as described herein and a pharmaceutically acceptable carrier and/or a pharmaceutically acceptable auxiliary substance.

One embodiment of the invention provides the use of a compound of formula I as described herein for the manufacture of a medicament for acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

One embodiment of the invention provides a method for the use of a compound as described herein, which is acting peripherally and centrally in the conditions of dysmenorrhea, male or female sexual dysfunction, hypertension, chronic heart failure, inappropriate secretion of vasopressin, liver cinthosis, nephrotic syndrome, anxiety, depressive disorders, obsessive compulsive disorder, autistic spectrum disorders, schizophrenia, and aggressive behavior, which method comprises administering said compound of formula I to a human being or animal.

Furthermore, the invention includes all optical isomers, i.e. diastereoisomers, diastereomeric mixtures, racemic mixtures, all their corresponding enantiomers and/or tautomers as well as their solvates of the compounds of formula I.

The compounds of formula I may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric centre of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

This applies in particular to the alkylcyclohexylether-head group (HG) of the compounds of formula I, namely

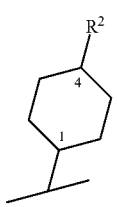

HG wherein at least the carbon atoms 1 and 4 are asymmetric carbon atoms and $R^2$ could further comprise asymmetric carbon atoms. It is to be understood that present invention includes all individual stereoisomers of head groups and mixtures thereof.

Examples of these head groups HG are depicted below, specific examples are HG-3 and HG-4, most specific is HG-4.

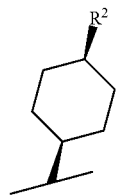

HG-1

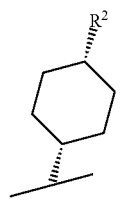

HG-2

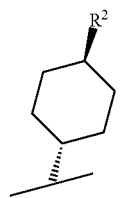

HG-3

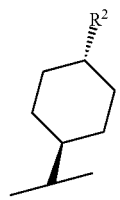

HG-4

It is further understood that all embodiments of the invention as described herein may be combined with each other.

In the embodiments, where optically pure enantiomers are provided, optically pure enantiomer means that the compound contains >90% of the desired isomer by weight, in particular >95% of the desired isomer by weight, or more particular >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

The compounds of formula I may be prepared in accordance with the following schemes. The starting material is commercially available or may be prepared in accordance with known methods. Any previously defined residues and variables will continue to have the previously defined meaning unless otherwise indicated.

The compounds of formula I can be prepared through a number of synthetic routes for example as illustrated in below schemes. The preparation of compounds of formula I of the present invention can be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes described below, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The processes are described in more detail with the following general schemes and procedures A to K.

Scheme 1: General Scheme A

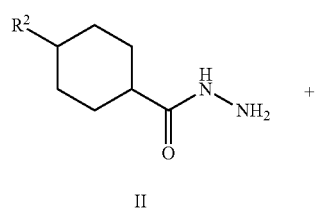

II

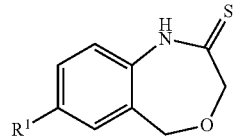

III

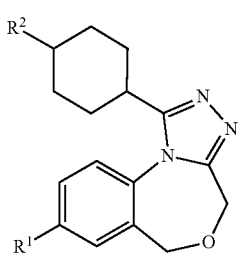

I

Compounds of formula (I) can be prepared by thermal condensation of a hydrazide derivative of formula (II) and a thiolactam derivative of formula (III). General scheme A is hereinafter further illustrated by general procedure (XI). The synthesis of compounds of formula (II) is outlined in general schemes C-K hereinafter. Compounds of formula (III) can be prepared following the general scheme B as described hereinafter.

Scheme 2: General Scheme B

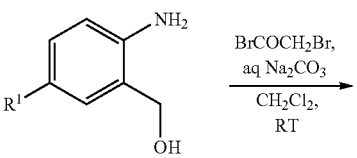

a

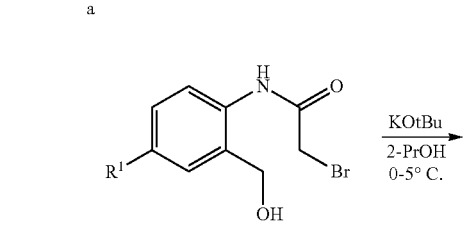

b

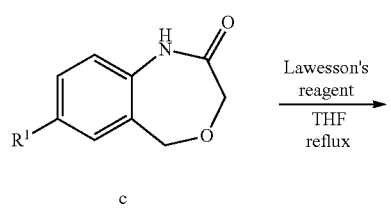

c

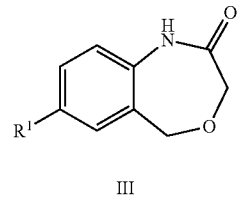

III

Thiolactam derivatives of formula (M) can be obtained as follows: Acylation of a 2-aminobenzyl alcohol of formula (a) to a bromo acetamide of formula (b) can be achieved under Schotten-Baumann conditions (e.g. 2-bromoacetyl bromide ($BrCOCH_2Br$), sodium carbonate ($Na_2CO_3$) in dichloromethyl ($CH_2Cl_2$) at room temperature (RT)) in quantitative yield. Cyclization of a compound of formula (b) with potassium tert-butoxide (KOtBu) in 2-propanol (2-PrOH) at low temperatures gives compounds of formula (c). A thiolactam derivative of formula (III) is obtained by treatment of a compound of formula (c) with Lawesson's reagent (2,4-bis-(4-methoxyphenyl)-1,3,2,4-dithiadiphosphetane-2,4-disulfide) or phosphorous pentasulfide at elevated temperature in an appropriate solvent (e.g. tetrahydrofurane (THF)).

Scheme 3: General Scheme C

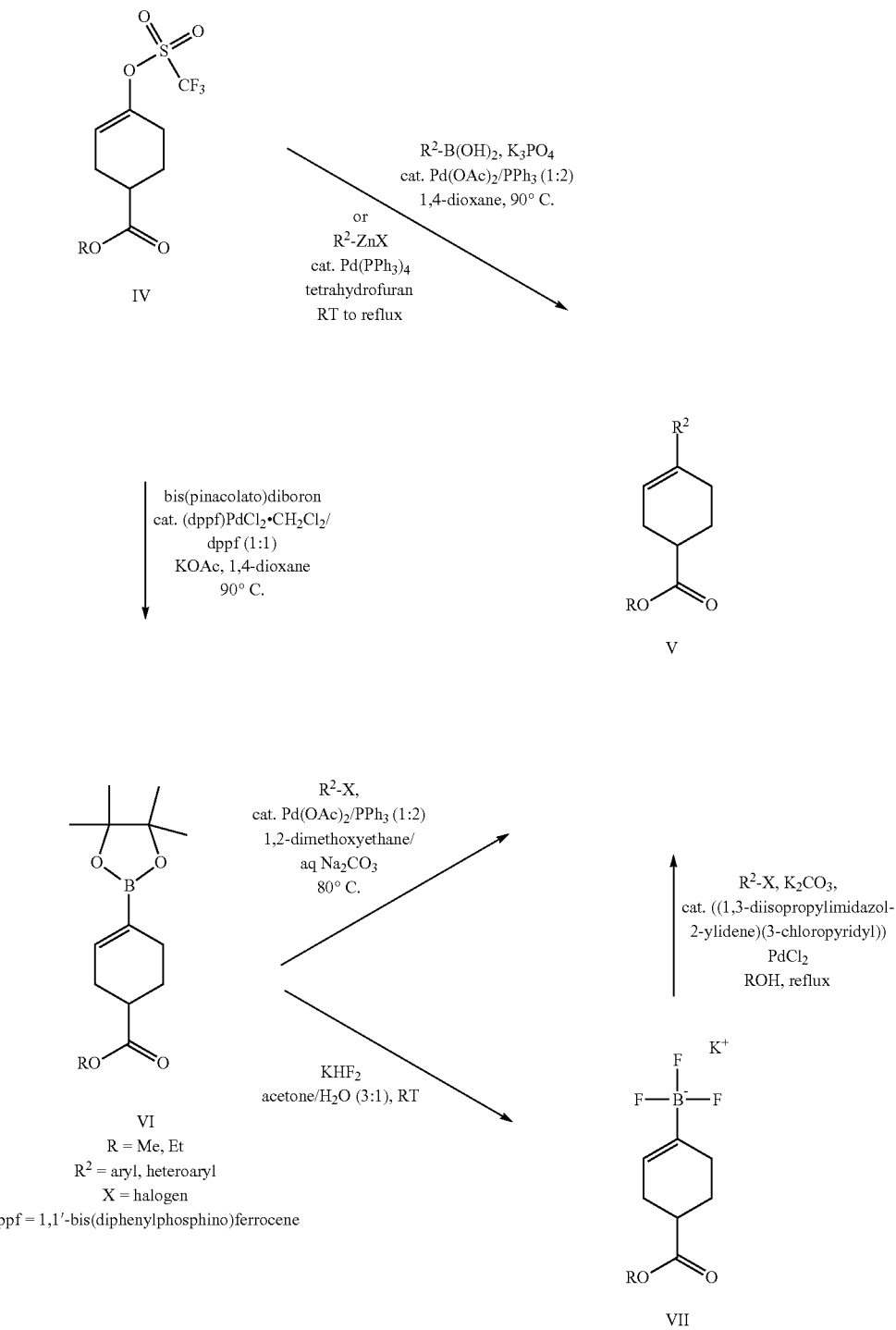

VI
R = Me, Et
R² = aryl, heteroaryl
X = halogen
dppf = 1,1'-bis(diphenylphosphino)ferrocene 4-Aryl- or 4-heteroaryl-cyclohex-3-enecarboxylic acid ester intermediates of formula (V) can be prepared under the conditions of the Suzuki reaction from a 4-trifluoromethanesulfonyloxy-cyclohex-3-enecarboxylic acid ester of formula (IV) and an aryl or heteroaryl boronic acid, an aryl or heteroaryl boronic acid ester or an aryl or heteroaryl trifluoroborate salt in a suitable organic solvent such as 1,4-dioxane, 1,2-dimethoxyethane, tetrahydrofuran or toluene in the presence of catalytic amounts of a 1:2 mixture of palladium(II) acetate and triphenylphosphine or a 1:1 mixture of palladium (II) acetate and a bisphosphine ligand or tetrakis(triphenylphosphine)palladium(0) and in the presence of a base such as an alkali metal salt of phosphate or carbonate, which is used neat or as an aqueous solution, at a reaction temperature between room temperature and reflux. Alternatively 4-aryl- or 4-heteroaryl-cyclohex-3-enecarboxylic acid ester intermediates of formula (V) can be prepared under the conditions of the Negishi reaction from a 4-trifluoromethanesulfonyloxy-cyclohex-3-enecarboxylic acid ester of formula (IV) and an aryl or heteroaryl zinc halide in a suitable organic solvent such as tetrahydrofuran and Pd(PPh)₃ at a reaction temperature between room temperature and reflux. Alternatively compounds of formula (V) can be prepared by coupling a potassium trifluoroborate salt of formula (VII) with an aryl or heteroaryl halide R²—X in the presence of a base such as potassium carbonate and a suitable palladium catalyst such as (1,3-diisopropylimidazol-2-ylidene)(3-chloropyridyl)palladium(II) chloride in a suitable solvent such as an alcohol at reflux. A potassium trifluoroborate salt of formula (VII) can be prepared by treatment of an (RS)-4-(4,4,5,5-tetramethyl-[1,3,2]dioxaborolan-2-yl)-cyclohex-3-enecarboxylic acid ester of formula (VI) with potassium hydrogen difluoride in a mixture of acetone and water at room temperature. Compounds of formula (VI) can be obtained by coupling a compound of formula IV with bis(pinacolato)diboron in the presence of a suitable base such as potassium acetate and a suitable palladium catalyst such as a 1:1 mixture of 1,1'-bis(diphenylphosphino)ferrocene and dichloro(1,1'-bis(diphenylphosphino)ferrocene)palladium(II) dichloromethane adduct in a suitable solvent such as 1,4-dioxane at 90° C. Compounds of formula (V) can alternatively be prepared under the conditions of the Suzuki reaction from a compound of formula (VI) and an aryl or heteroaryl halide R²—X in a suitable organic solvent such as 1,4-dioxane, 1,2-dimethoxyethane, tetrahydrofuran or toluene in the presence of catalytic amounts of a 1:2 mixture of palladium(II) acetate and triphenylphosphine or a 1:1 mixture of palladium(II) acetate and a bisphosphine ligand or tetrakis(triphenylphosphine)palladium(0) and in the presence of a base such as an alkali metal salt of phosphate or carbonate, which is used neat or as an aqueous solution, at a reaction temperature between room temperature and reflux. General scheme C is hereinafter further illustrated by general procedure (I).

Scheme 4: General Scheme D

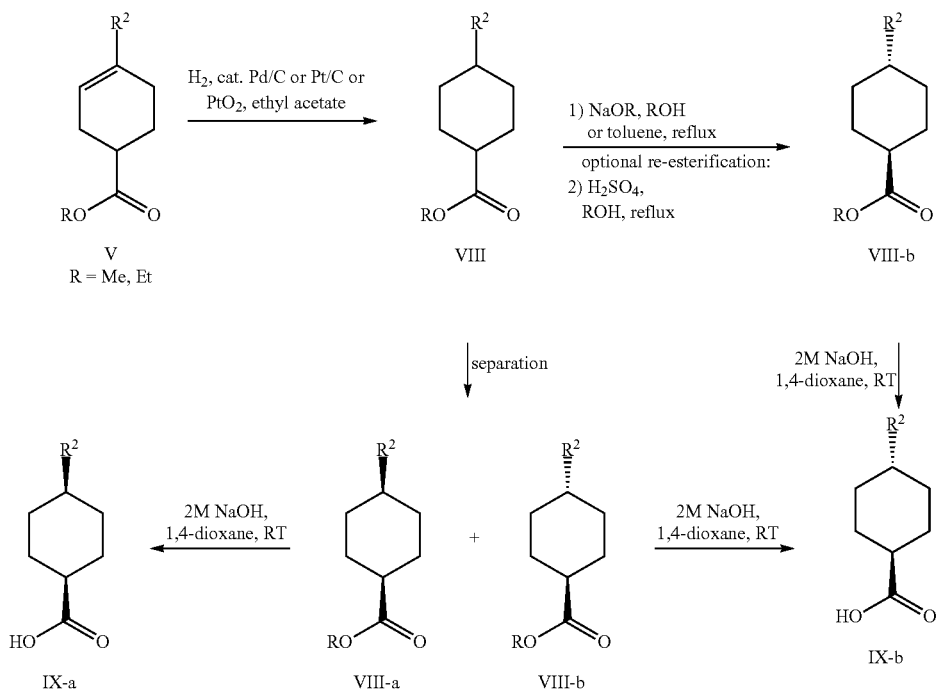

4-Substituted cyclohexane carboxylic acid ester intermediates of formula (VIII) are usually obtained as a mixture of the cis and the trans isomer by reduction of 4-substituted cyclohex-3-enyl carboxylic acid ester intermediates of formula (V) under an atmosphere of hydrogen gas (1 bar) in a suitable solvent such as ethyl acetate or an alcohol in the presence of a catalytic amount of palladium or platinum on charcoal or platinum(IV) oxide at room temperature. Compounds of formula (V) and (VIII), the residue R² of which is an aryl group substituted with one or more halide substituents other than fluorine may undergo partial or complete dehalogenation under these reaction conditions. The acid formed as a consequence of the dehalogenation reaction may be neutralized by addition of a base such as a trialkyl amine to the reaction mixture. Pretreatment of the palladium or platinum catalyst with a zinc halide may in some cases prevent or reduce dehalogenation of compounds of formula (V) and (VIII), the residue R² of which is an aryl group substituted with one or more halide substituents other than fluorine. Cis/trans mixtures of 4-substituted cyclohexane carboxylic acid ester intermediates of formula (VIII) may in some cases be separable by the usual methods such as silica gel column or high performance chromatography or crystallization into pure cis-4-substituted cyclohexane carboxylic acid ester intermediates of formula (VIII-a) and trans-4-substituted cyclohexane carboxylic acid ester intermediates of formula (VIII-b), which can be saponified to pure cis-4-substituted cyclohexane carboxylic acid intermediates of formula (IX-a) and trans-4-substituted cyclohexane carboxylic acid intermediates of formula (IX-b) under standard conditions such as stirring in a mixture of aqueous sodium hydroxide solution and an etheral solvent such as 1,4-dioxane, tetrahydrofuran or diethyl ether a room temperature. Alternatively, trans-4-substituted cyclohexane carboxylic acid intermediates of formula (IX-b) can be obtained by epimerization of the cis isomer of cis/trans-mixtures of 4-substituted cyclohexane carboxylic acid ester intermediates of formula (VIII) using a suitable base, e.g. an alkali metal alkoxide such as sodium or potassium methylate or ethylate, in a suitable solvent such as methanol, ethanol or toluene at reflux followed by saponification of the crude reaction mixture, which may consist of a mixture of a trans-4-substituted cyclohexane carboxylic acid intermediate of formula (IX-b) and a trans-4-substituted cyclohexane carboxylic acid ester intermediate of formula (VIII-b), under standard conditions such as stirring in a mixture of aqueous sodium hydroxide solution and an etheral solvent such as 1,4-dioxane, tetrahydrofuran or diethyl ether at room temperature. In case the epimerization reaction was carried out in an alcohol as solvent, the crude reaction mixture can alternatively be acidified by the addition of concentrated sulfuric acid and heated to reflux to obtain a trans-4-substituted cyclohexane carboxylic acid ester intermediate of formula (VIII-b). General scheme D is hereinafter further illustrated with general procedures (V) and (VI).

Scheme 5: General Scheme E

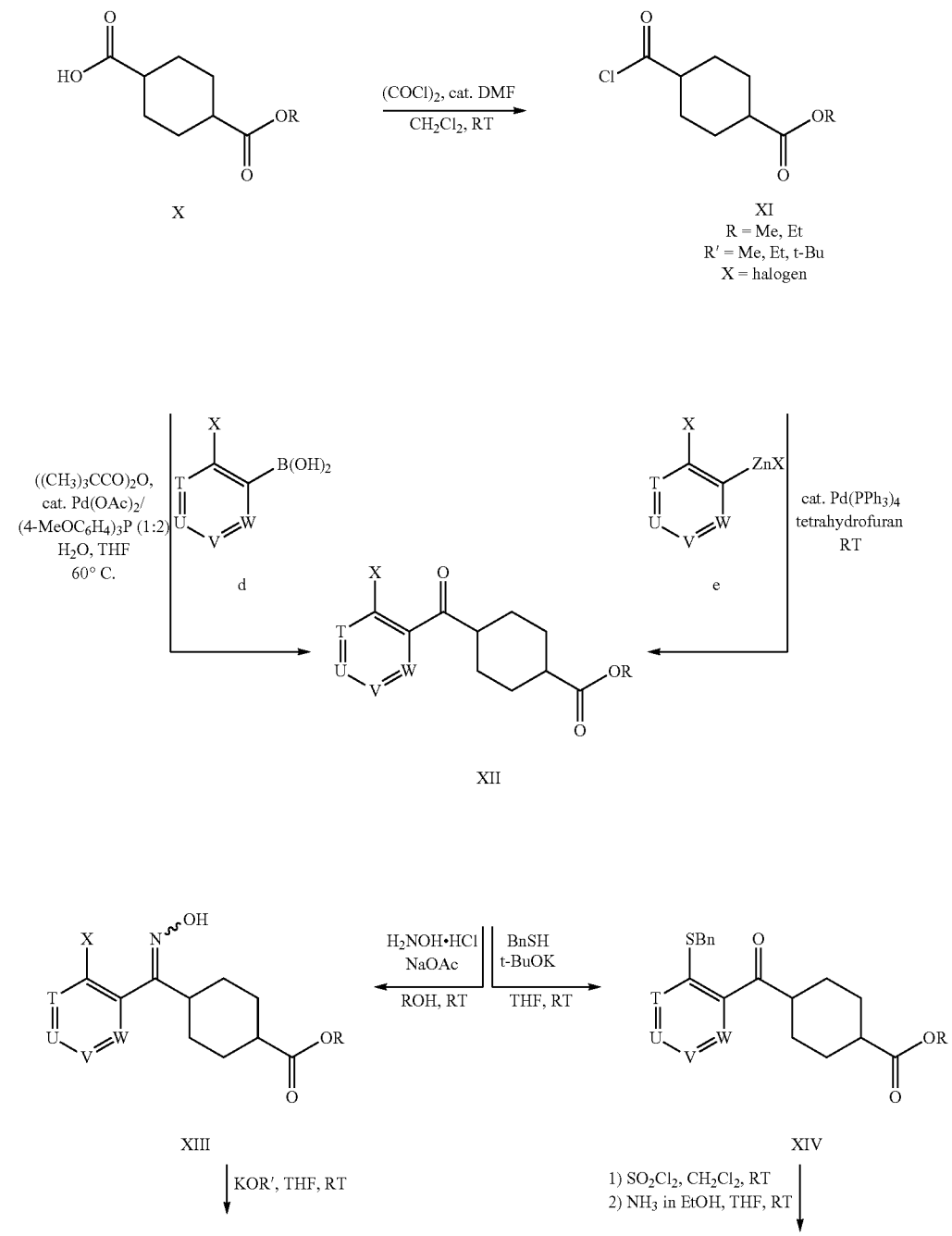

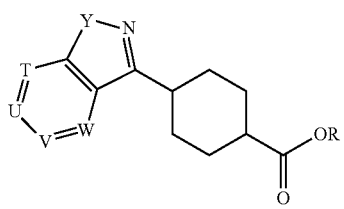

VIII-1 (Y = O)

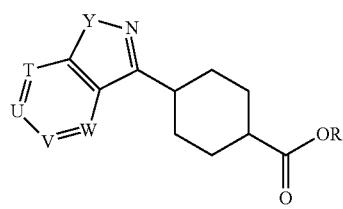

VIII-2 (Y = S)

T, U, V, W = C-Ra or N, with Ra = H, OH halogen, cyano, C1-6-alkyl, C1-6-alkoxy, halogen-C1-6-alkyl, halogen-C1-6-alkoxy or hydroxy-C1-6-alkyl 4-Aroyl-cyclohexanecarboxylic acid ester intermediates of formula (XII) can be prepared by coupling a cyclohexane-1,4-dicarboxylic acid monoester of formula (X) with an aryl or heteroaryl boronic acid of formula (d) in the presence of a carboxylic acid anhydride such as trimethylacetic anhydride and a suitable palladium catalyst such as a mixture of palladium(II) acetate and a phosphine ligand, e.g. tris(4-methoxyphenyl)phosphine, in tetrahydrofuran containing a small amount of water at 60° C. Alternatively, 4-aroyl-cyclohexanecarboxylic acid ester intermediates of formula (XII) can be synthesized by coupling a 4-chlorocarbonyl-cyclohexanecarboxylic acid ester of formula (XI), which can be obtained from a cyclohexane-1,4-dicarboxylic acid monoester of formula (X) by methods known in the art for the conversion of carboxylic acids to carboxylic acid chlorides such as treatment with thionyl chloride or oxalyl chloride and a catalytic amount of N,N-dimethylformamide, with an aryl or heteroaryl zinc halide of formula (e) in the presence of a suitable palladium catalyst such as tetrakis(triphenylphosphine)palladium(0) in tetrahydrofuran at room temperature. Treatment of a 4-aroyl-cyclohexanecarboxylic acid ester intermediate of formula (XII) with a mixture of hydroxylamine hydrochloride and sodium acetate in a suitable alcohol at room temperature gives rise to an oxime intermediate of formula (XIII), which is usually obtained as an E/Z mixture. An oxime intermediate of formula (XIII) can be cyclized to an aryl or heteroaryl isoxazole intermediate of formula (VIII-1) by treatment with a potassium alkoxide base in tetrahydrofuran at room temperature. Alternatively, treatment of a 4-aroyl-cyclohexanecarboxylic acid ester intermediate of formula (XII) with benzyl mercaptane and potassium tert-butoxide in tetrahydrofuran at room temperature leads to a benzyl ether of formula (XIV), which can be cyclized to an aryl or heteroaryl isothiazole intermediate of formula (VIII-2) via consecutive S-debenzylation with sulfuryl chloride in dichloromethane at room temperature and treatment with an ethanolic solution of ammonia in tetrahydrofuran at room temperature. General scheme E is hereinafter further illustrated with general procedures (II), (III), (IV), (VII) and (VIII).

Scheme 6: General Scheme F

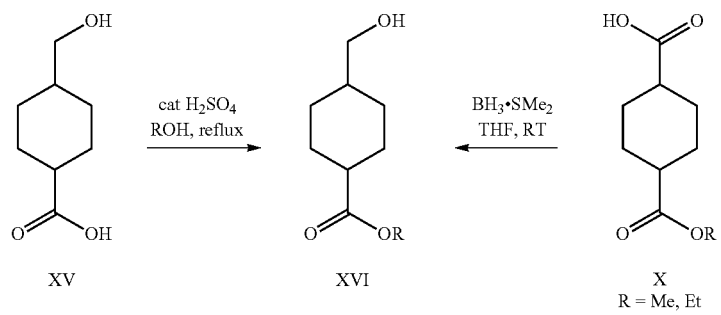

XV

XVI

X
R = Me, Et (COCl)$_2$, DMSO,
Et$_3$N, CH$_2$Cl$_2$,
-78° C. to RT

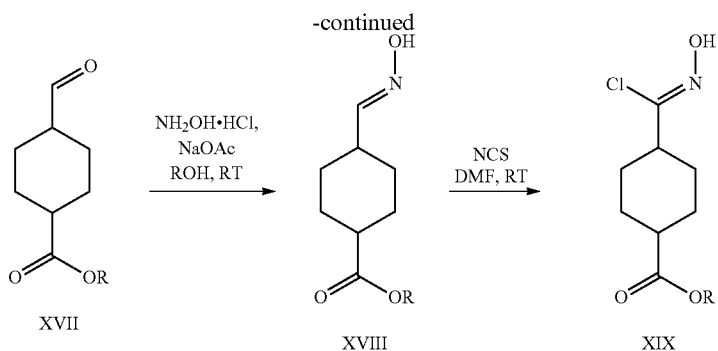

A 4-hydroxymethyl-cyclohexanecarboxylic acid ester of formula (XVI) can either be prepared by esterification of 4-hydroxymethyl-cyclohexanecarboxylic acid (XV) in an alcohol in the presence of a catalytic amount of an acid such as concentrated sulfuric acid at elevated temperature, usually reflux, or by reduction of a cyclohexane-1,4-dicarboxylic acid mono ester of formula (X) using the usual methods known in the art, e.g. a borane derivative such as borane-dimethylsulfide complex. An alcohol intermediate of formula (XVI) can be oxidized to an aldehyde intermediate of formula (XVII) using the usual methods known in the art for the oxidation of a primary alcohol group, e.g. treatment with oxalyl chloride, DMSO and a base such as triethylamine. A hydroxamoyl chloride intermediate of formula (XIX) can be prepared by chlorination of an aldoxime intermediate of formula (XVIII), which can be obtained by treatment of an aldehyde intermediate of formula (XVII) with hydroxylamine hydrochloride in the presence of sodium acetate.

Scheme 7: General Scheme G

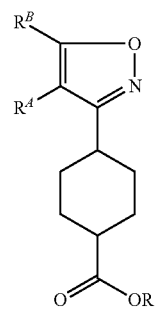

VIII-3

R = Me, Et
$R^A$ = H, $C_{1-6}$-alkyl
$R^B$ = $C_{1-6}$-alkyl,
or $R^A$ and $R^B$ form a ring
R″ = optionally substituted $C_{1-6}$-alkyl or aryl An isoxazole intermediate of formula (VIII-3) may be obtained by 3+2 cyclization of a nitrile oxide, which is formed in situ by elimination of hydrochloric acid from a hydroxamoyl chloride intermediate of formula (XIX) in the presence of a base such as triethyl amine, with an enol ester intermediate of formula (f) followed by spontaneous elimination of a carboxylic acid R″COOH under the reaction conditions.

Scheme 8: General Scheme H

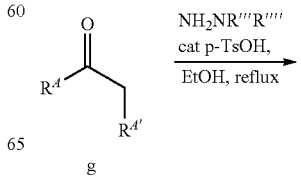

-continued

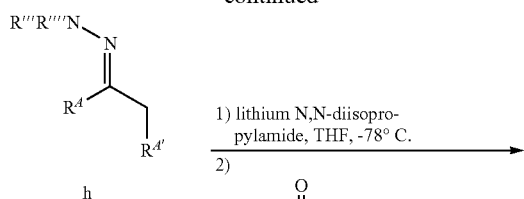

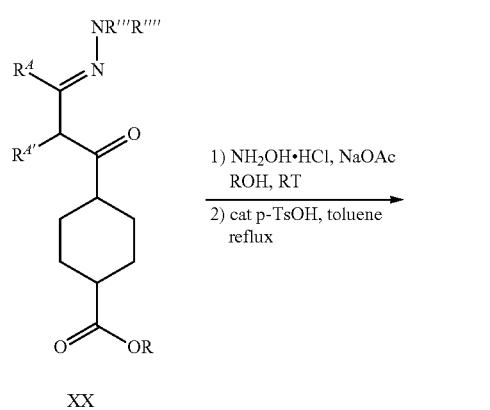

R = Me, Et
$R^A$, $R^{A'}$ = H, $C_{1-6}$-alkyl, or $R^A$ and $R^{A'}$ form a ring
$R'''$, $R''''$ = $C_{1-6}$-alkyl, or $R''''$ and $R'''''$ form a ring Isoxazole intermediates of formula (VIII-4) may be obtained from intermediates of formula (XX) by consecutive treatment with hydroxyl amine hydrochloride and sodium acetate and heating at reflux in toluene in the presence of a catalytic amount of para-toluenesulfonic acid. Compounds of formula (XX) can be obtained by deprotonation of a hydrazone of formula (h) with a strong base such as lithium N,N-diisopropylamide at low temperature followed by acylation with a compound of formula (XI). Compounds of formula (h) can be obtained from a ketone of formula (g) by the usual methods, e.g. by treatment with a hydrazine derivative $NH_2$—NR'''R'''' in the presence of a catalytic amount of an acid such as para-toluenesulfonic acid in a suitable solvent such as ethanol.

Scheme 9: General Scheme I

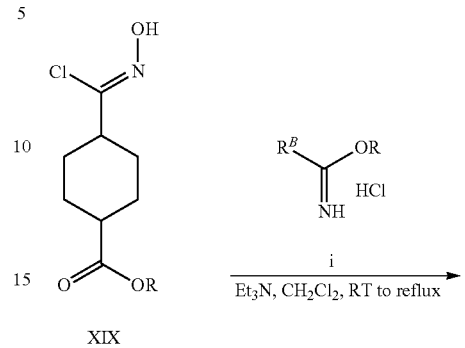

R = Me, Et
$R^B = C_{1-6}$-alkyl

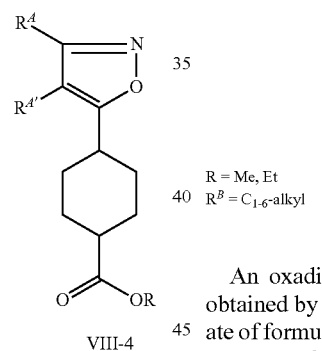

An oxadiazole intermediate of formula (VIII-5) can be obtained by treatment of a hydroxamoyl chloride intermediate of formula (XIX) with an imidate salt of formula (i) in the presence of a base such as triethylamine in a suitable solvent such as dichloromethane.

Scheme 10: General Scheme J

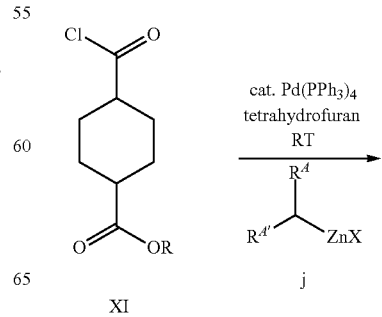

-continued

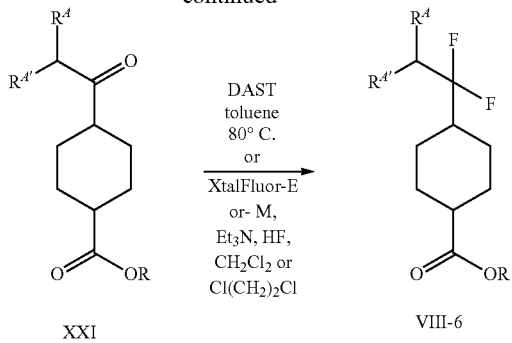

XXI

R = Me, Et
$R^4, R^{4'}$ = H, $C_{1-6}$-alkyl,
or $R^4, R^{4'}$ form a ring

VIII-6

4-(1,1-Difluoro-alkyl)-cyclohexanecarboxylic acid ester intermediates of formula (VIII-6) can be prepared by coupling an acid chloride of formula (XI) with an alkyl zinc halide of formula (j) in the presence of a suitable palladium catalyst such as tetrakis(triphenylphosphine)palladium(0) in tetrahydrofuran at room temperature followed by treatment of the resulting 4-(alkyl-carbonyl)-cyclohexanecarboxylic acid ester intermediate of formula (XXI) with a fluorinating reagent such as DAST in toluene at 80° C. or XtalFluor-E ((diethylamino)difluorosulfonium tetrafluoroborate) or XtalFluor-M (difluoro(mopholino)sulfonium tetrafluoroborate) in dichloromethane or dichioroethane in the presence of an amine such as triethylamine and HF at a suitable reaction temperature.

Scheme 11: General Scheme K

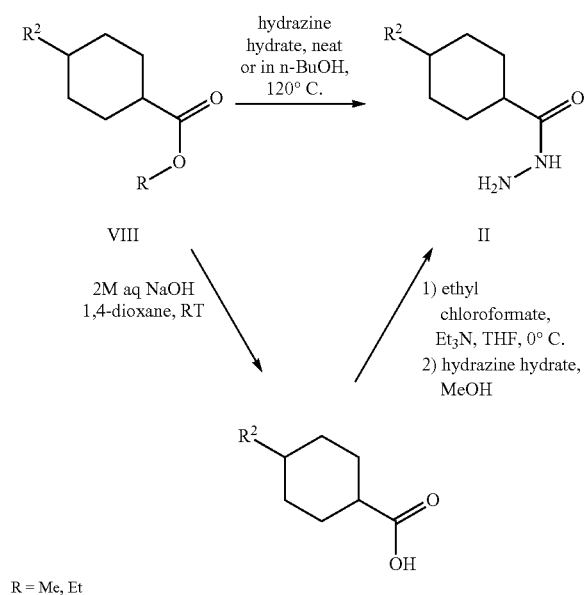

R = Me, Et

A 4-heteroaryl-cyclohexanecarboxylic acid ester intermediate of formula (VIII) can be converted to a hydrazide of formula (II) by heating with hydrazine hydrate. Alternatively, an ester of formula (VIII) can be hydrolyzed to a carboxylic acid of formula (IX) using a biphasic mixture of aqueous sodium or potassium hydroxide solution and an etheral solvent such as dioxane, tetrahydrofuran or diethyl ether. A hydrazide of formula (II) can be obtained by activating an acid intermediate of formula (IX), e.g. with ethyl chloroformate, thionyl chloride, oxalyl chloride or a peptide coupling reagent, and subsequent coupling with hydrazine. General scheme F is hereinafter further illustrated with general procedures (VII) and (VIII).

The corresponding pharmaceutically acceptable salts with acids can be obtained by standard methods known to the person skilled in the art, e.g. by dissolving the compound of formula I in a suitable solvent such as e.g. dioxan or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts are hydrochloride, formate and trifluoroacetate.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of general formula I in this invention may be derivatised at functional groups to provide derivatives which are capable of conversion back to the parent compound in vivo.

Pharmacological Tests

The human V1a receptor was cloned by RT-PCR from total human liver RNA. The coding sequence was subcloned in an expression vector after sequencing to confirm the identity of the amplified sequence. To demonstrate the affinity of the compounds from the present invention to the human V1a receptor binding studies were performed. Cell membranes were prepared from HEK293 cells transiently transfected with the expression vector and grown in 20 liter fermenters with the following protocol.

50 g of cells are resuspended in 30 ml freshly prepared ice cold Lysis buffer (50 mM HEPES, 1 mM EDTA, 10 mM $MgCl_2$ adjusted to pH=7.4+complete cocktail of protease inhibitor (Roche Diagnostics)). Homogenized with Polytron for 1 min and sonicated on ice for 2×2 minutes at 80% intensity (Vibracell sonicator). The preparation is centrifuged 20 min at 500 g at 4° C., the pellet is discarded and the supernatant centrifuged 1 hour at 43'000 g at 4° C. (19,000 rpm). The pellet is resuspended in 12.5 ml Lysis buffer+12.5 ml Sucrose 20% and homogenized using a Polytron for 1-2 min. The protein concentration is determined by the Bradford method and aliquots are stored at −80° C. until use. For binding studies 60 mg Yttrium silicate SPA beads (Amersham) are mixed with an aliquot of membrane in binding buffer (50 mM Tris, 120 mM NaCl, 5 mM KCl, 2 mM $CaCl_2$, 10 mM $MgCl_2$) for 15 minutes with mixing. 50 µl of bead/membrane mixture is then added to each well of a 96 well plate, followed by 50 µl of 4 nM 3H-Vasopressin (American Radiolabeled Chemicals). For total binding measurement 100 µl of binding buffer are added to the respective wells, for non-specific binding 100 µl of 8.4 mM cold vasopressin and for compound testing 100 µl of a serial dilution of each compound in 2% DMSO. The plate is incubated 1 h at room temperature, centrifuged 1 min at 1000 g and counted on a Packard Top-Count. Non-specific binding counts are subtracted from each well and data is normalized to the maximum specific binding set at 100%. To calculate an IC 50 the curve is fitted using a non-linear regression model (XLfit) and the Ki is calculated using the Cheng-Prussoff equation.

The following representative data show the antagonistic activity against human V1a receptor of compounds according to present invention:

TABLE 1 pKi values of selected examples

| Ex. | Structure | pKi hV1a |
|---|---|---|
| 1 | | 8.62 |
| 2 | | 8.13 |
| 3 | | 9.54 |
| 4 | 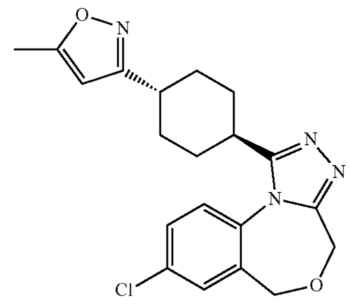 [SMILES: Cc1cc([C@H]2CC[C@H](c3nnc4n3-c3ccc(Cl)cc3COC4)CC2)no1] | 8.4 |
| 5 | 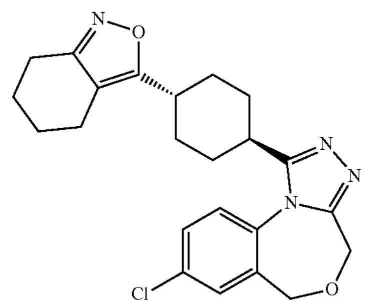 [SMILES: Clc1ccc2c(c1)COCc1nnc([C@H]3CC[C@H](c4onc5c4CCCC5)CC3)n1-2] | 7.81 |
| 6 | 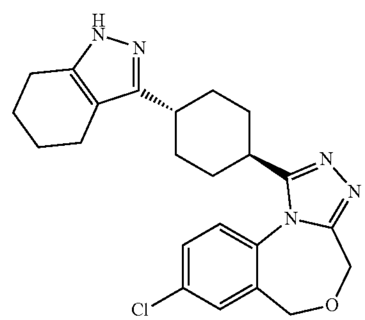 [SMILES: Clc1ccc2c(c1)COCc1nnc([C@H]3CC[C@H](c4n[nH]c5c4CCCC5)CC3)n1-2] | 8.31 |
| 7 | 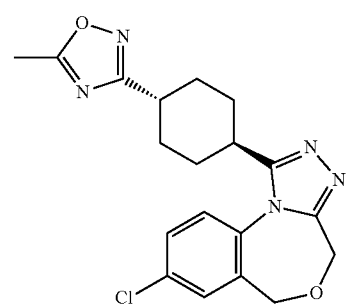 [SMILES: Cc1nc([C@H]2CC[C@H](c3nnc4n3-c3ccc(Cl)cc3COC4)CC2)no1] | 7.49 |
| 8 | 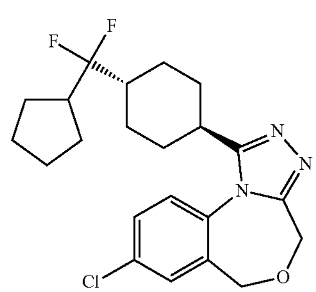 [SMILES: FC(F)(C1CCCC1)[C@H]1CC[C@H](c2nnc3n2-c2ccc(Cl)cc2COC3)CC1] | 8.62 |

TABLE 1-continued pKi values of selected examples

| Ex. | Structure | pKi hV1a |
|---|---|---|
| 9 | (structure shown) | 7.59 |

Pharmaceutical Compositions

The compounds of formula I and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, in particular 1-100 mg, of a compound of formula I. Examples of compositions according to the invention are:

Example A

Tablets of the following composition are manufactured in the usual manner:

TABLE 2 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 3 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example 13-2

Soft Gelatin Capsules of the following composition are manufactured:

TABLE 4

| possible soft gelatin capsule ingredient composition | |
|---|---|
| ingredient | mg/capsule |
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 5

| possible soft gelatin capsule composition | |
|---|---|
| ingredient | mg/capsule |
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 6

| possible suppository composition | |
|---|---|
| ingredient | mg/supp. |
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 7

| possible injection solution composition | |
|---|---|
| ingredient | mg/injection solution. |
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 8

| possible sachet composition | |
|---|---|
| ingredient | mg/sachet |
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples are provided for illustration of the invention. They should not be considered as limiting the scope of the invention, but merely as being representative thereof.

Thiolactam Intermediates of Formula (III)

7-Chloro-3,5-dihydrobenzo[e][1,4]oxazepine-2(1H)-thione a) 2-Bromo-N-(4-chloro-2-(hydroxymethyl)phenyl)acetamide To a mixture of (2-amino-5-chlorophenyl)methanol (4.30 g, 27.3 mmol) in dichloromethane (220 ml) was added 2-bromoacetyl bromide (6.06 g, 2.61 ml, 30.0 mmol) at 0-5° C. Stirring for 5 minutes was followed by dropwise addition of aqueous 2 M sodium carbonate solution (130 ml) in approx. 10 minutes. The cooling bath was removed and stirring was continued for 2 h. The solvent was concentrated in vacuo. The aqueous residue was extracted with three 100 ml-portions of ethyl acetate. The combined organic layers were washed with one 50 ml-portion of brine, dried over anhydrous sodium sulfate and concentrated in vacuo to give the title compound (7.30 g, 96%) as light grey solid which was used in the next step without purification. MS m/e: 276 ([M+1−1]+).

b) 7-Chloro-3,5-dihydrobenzo[e][1,4]oxazepin-2 (1H)-one

To a suspension of 2-bromo-N-(4-chloro-2-(hydroxymethyl)phenyl)acetamide (3.60 g, 12.9 mmol) in 2-propanol (129 ml) was added in small portions potassium tert-butoxide (3.77 g, 33.6 mmol) at 0-5° C. The reaction mixture was stirred for 90 minutes and then poured on ice/water (500 ml). The precipitate was collected by filtration and washed with water. Residual water was removed by evaporation of two 50 ml-portions of toluene to give the title compound (2.34 g, 92%) as light yellow solid. MS m/e: 196 ([M−H]−).

c) 7-Chloro-3,5-dihydrobenzo[e][1,4]oxazepine-2 (1H)-thione

To a suspension of 7-chloro-3,5-dihydrobenzo[e][1,4]oxazepin-2(1H)-one (3.01 g, 15.2 mmol) in tetrahydrofurane (102 ml) was added 2,4-bis-(4-methoxyphenyl)-1,3,2,4-dithiadiphosphetane-2,4-disulfide (3.45 g, 8.53 mmol) at room temperature. The reaction mixture was heated at reflux for 4 h. The solvent was evaporated and the residue was crystallized from hot ethanol to give the title compound (1.96 g, 60%) as light yellow solid. MS m/e: 211.6 ([M−H]−).

Intermediate Formula (IV)

(RS)-4-Trifluoromethanesulfonyloxy-cyclohex-3-enecarboxylic acid ethyl ester

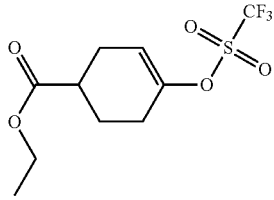 [SMILES: CCOC(=O)C1CC=C(OS(=O)(=O)C(F)(F)F)CC1]

To a solution of ethyl-4-cyclohexanonecarboxylate (25.0 g, 147 mmol) in tetrahydrofuran (580 ml) was added a 1M solution of lithium bis(trimethylsilyl)amid in tetrahydrofuran (154 ml, 154 mmol) at −78° C. Stirring for 1 h was followed by addition of a solution of N-phenyl-bis(trifluoromethanesulfonimide) (55.1 g, 154 mmol) in tetrahydrofuran (80 ml). The cooling bath was removed 30 minutes after completed addition, and the reaction mixture was stirred for 12 h at room temperature. The mixture was quenched with 1 M aqueous sodium hydrogen sulfate solution (154 ml, 154 mmol). The solvent was removed by rotary evaporation (water bath of 40° C.). The residue was partitioned between tert-butyl methyl ether (500 ml) and 0.5 M aqueous sodium hydroxide solution (400 ml). The organic layer was washed with two 400-ml portions of 0.5 M aqueous sodium hydroxide solution, one 200-ml portion of saturated ammonium chloride solution and one 100-ml portion of brine, dried over anhydrous sodium sulfate and concentrated in vacuo to give the title compound (41.8 g, 94.2%) as yellow oil, which was used in the following steps without further purification. MS m/e: 273 ([M−C$_2$H$_5$]−).

Intermediate of Formula (VI)

(RS)-4-(4,4,5,5-Tetramethyl-[1,3,2]dioxaborolan-2-yl)-cyclohex-3-enecarboxylic acid ethyl ester

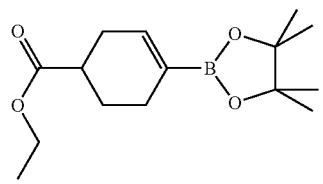 [SMILES: CCOC(=O)C1CC=C(B2OC(C)(C)C(C)(C)O2)CC1]

A mixture of (RS)-4-trifluoromethanesulfonyloxy-cyclohex-3-enecarboxylic acid ethyl ester (3.0 g, 9.92 mmol), potassium acetate (2.92 g, 29.8 mmol) and bis(pinacolato)diboron (3.78 g, 14.9 mmol) in 1,4-dioxane (30 ml) was purged with argon. Addition of 1,1'-bis(diphenylphosphino)ferrocene (0.17 g, 0.30 mmol) and dichloro(1,1'-bis(diphenylphosphino)ferrocene)palladium(II) dichloromethane adduct (0.22 g, 0.30 mmol) was followed by stirring at 90° C. for 18 h. The reaction mixture was partitioned between ethyl acetate (200 ml) and water (150 ml). The layers were separated. The organic layer was washed with one portion of brine, dried over anhydrous sodium sulfate and concentrated to dryness. Flash-chromatography with n-heptane/ethyl acetate as eluent gave the title compound (1.95 g, 70%) as light yellow oil. MS m/e: 281 ([M+H]+)

Intermediate of Formula (VII)

Potassium (RS)-(4-(ethoxycarbonyl)cyclohex-1-enyl)trifluoroborate

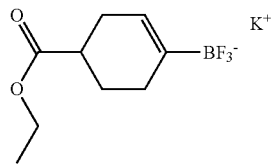

To a solution of (RS)-4-(4,4,5,5-tetramethyl-[1,3,2]dioxaborolan-2-yl)-cyclohex-3-enecarboxylic acid ethyl ester (0.37 g, 1.32 mmol) in acetone (9 ml) and water (3 ml) was added potassium hydrogen difluoride (0.41 g, 5.28 mmol). Stirring for 4 h at room temperature was followed by evaporation of the solvent mixture. The residue was triturated in warm acetonitrile (20 ml). The solids were removed by filtration. The filtrate was concentrated to dryness to give the title compound (0.35 g, quantitative) as white solid which was used without further purification in the next step.

4-Aryl- and 4-heteroaryl-cyclohex-3-enecarboxylic acid ester intermediates of formula (V)

General Procedure (I):

To a mixture of potassium (RS)-(4-(ethoxycarbonyl)cyclohex-1-enyl)trifluoroborate (1 eq), an aryl or heteroaryl halide (1.2 eq) and potassium carbonate (3 eq) in an alcohol such as ethanol or methanol (0.2 M) is added (1,3-diisopropylimidazol-2-ylidene)(3-chloropyridyl)palladium (II) chloride (0.02 eq). The mixture is stirred at reflux for 1-20 h. After cooling to room temperature the solvent is evaporated. The residue is triturated in an organic solvent such as tert-butyl methyl ether or ethyl acetate. The precipitates are removed by filtration. The filtrate is concentrated to dryness. Purification by flash-chromatography gives a 4-aryl- or 4-heteroaryl-cyclohex-3-enecarboxylic acid ester intermediate of formula (V).

(RS)-4-(3-Fluoro-pyridin-2-yl)-cyclohex-3-enecarboxylic acid ethyl ester

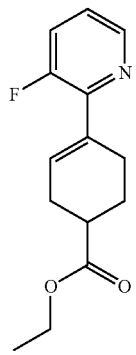

The title compound was obtained as colorless oil in 89% yield from 2-bromo-3-fluoropyridine according to general procedure (I). MS m/e: 250 ([M+H]$^+$).

Intermediate of Formula (XI)

trans-4-Chlorocarbonyl-cyclohexanecarboxylic acid methyl ester

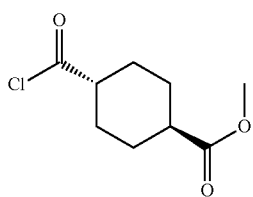

To a solution of trans-1,4-cycloxanedicarboxylic acid monomethylester (2.0 g, 11 mmol) in dichloromethane (30 ml) was added oxalyl chloride (1.1 ml, 13 mmol) and a catalytic amount of N,N-dimethylformamide at 0-5°. The cooling bath was removed, and the reaction mixture was stirred for 24 h at room temperature. After evaporation of the solvent the residue was triturated in n-hexane (100 ml). The precipitate was removed by filtration. The filtrate was concentrated in vacuo to give the title compound (2.2 g, quantitative) as colorless oil which was used in the next step without further purification.

4-Aroyl-cyclohexanecarboxylic acid ester intermediates of formula (XII)

General Procedure (II): Negishi Coupling

To a solution of an aryl or heteroaryl bromide (1 eq) in dry tetrahydrofuran (0.2 M) is added a 2M isopropyl magnesium chloride solution in tetrahydrofuran (1.05 eq) at 0-5° C. The cooling bath is removed and the reaction mixture is stirred for 1 h at room temperature. A solution of zinc chloride (2 eq), which is previously dried by melting in vacuo followed by cooling under argon, in dry tetrahydrofuran (1.0 M) is added to the Grignard intermediate. Stirring for 1 h is followed by addition of 4-chlorocarbonyl-cyclohexanecarboxylic acid methyl ester (1 eq) and tetrakis(triphenylphosphine)palladium(0) (0.05 eq). The reaction mixture is quenched with aqueous saturated ammonium chloride solution after 18-24 h and extracted with two or three portions of an organic solvent such as tert-butyl methyl ether or ethyl acetate. The combined organic layers are dried over anhydrous sodium sulfate and concentrated to dryness. Purification by flash-chromatography gives a 4-aroyl-cyclohexanecarboxylic acid ester intermediate of formula (XII).

trans-4-(2-Fluoro-benzoyl)-cyclohexanecarboxylic acid methyl ester

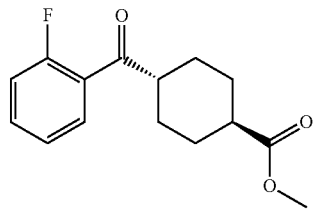 [SMILES: COC(=O)[C@H]1CC[C@H](C(=O)c2ccccc2F)CC1]

The title compound was obtained as colorless liquid in 32% yield from 1-bromo-2-fluorobenzene according to general procedure (II). MS m/e: 264 (M+)

Oxime Intermediates of Formula (XIII)

General Procedure (III): Oxime Formation

A mixture of a 4-aroyl-cyclohexanecarboxylic acid ester of formula XII (1 eq), sodium acetate (2.4 eq) and hydroxylamine hydrochloride (2.4 eq) in an alcohol such as methanol or ethanol (0.1-0.2 M) is stirred at room temperature for 2-24 h. The reaction mixture is optionally concentrated to dryness or directly partitioned between an organic solvent such as ethyl acetate or tert-butyl methyl ether and 2M aqueous sodium carbonate solution. The layers are separated. The aqueous layer is extracted with one or two portions of organic solvent. The combined organic layers are dried over anhydrous sodium sulfate and concentrated to dryness. Purification by flash-chromatography gives an oxime intermediate of formula (XIII).

trans-4-{(2-Fluoro-phenyl)-[(E/Z)-hydroxyimino]-methyl}-cyclohexanecarboxylic acid methyl ester

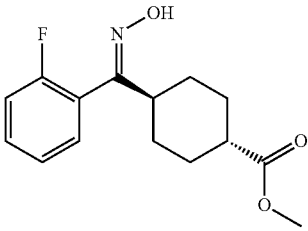 [SMILES: COC(=O)[C@H]1CC[C@H](/C(=N\O)c2ccccc2F)CC1]

The title compound was obtained as white solid in 98% yield from trans-4-(2-fluoro-benzoyl)-cyclohexanecarboxylic acid methyl ester according to general procedure (III). MS m/e: 280 ([M+H]$^+$)

Thioether Intermediates of Formula (XIV)

General Procedure (IV): Thioether Formation

A mixture of potassium tert-butoxide (1 eq) and benzyl mercaptane (1.1 eq) in dry tetrahydrofuran (0.3 M) is stirred for 5 min at room temperature under an inert gas atmosphere. A solution of a 4-aroyl-cyclohexanecarboxylic acid ester intermediate of formula (XII) (1 eq) in tetrahydrofuran (0.3 M) is added and the reaction mixture is stirred for 16-24 h. The reaction mixture is partitioned between an organic solvent such as ethyl acetate or tert-butyl methyl ether and water. The layers are separated. The aqueous layer is extracted with one or two portions of organic solvent. The combined organic layers are dried over anhydrous sodium sulfate and concentrated to dryness. Purification by flash-chromatography gives a thioether intermediate of formula (XIV).

trans-4-(2-Benzylsulfanyl-benzoyl)-cyclohexanecarboxylic acid methyl ester

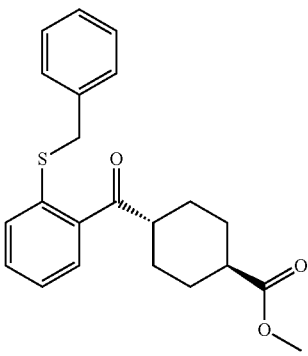 [SMILES: COC(=O)[C@H]1CC[C@H](C(=O)c2ccccc2SCc2ccccc2)CC1]

The title compound was obtained as yellow oil in 92% yield from trans-4-(2-fluoro-benzoyl)-cyclohexanecarboxylic acid methyl ester according to general procedure (IV). MS m/e: 369 ([M+H]$^+$)

Intermediates of Formula (XVI)

trans-4-Hydroxymethyl-cyclohexanecarboxylic acid methyl ester

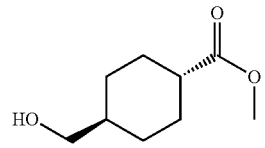

To a solution of trans-4-(methoxycarbonyl)cyclohexanecarboxylic acid (10.0 g, 53.7 mmol) in tetrahydrofuran (540 ml) was added borane-dimethylsulfide complex (6.80 g, 80.6 mmol) at 0-5° C. The cooling bath was removed after 15 minutes and the mixture was stirred for 4 h. The reaction mixture was quenched with methanol (17.2 g, 537 mmol), stirred for 20 minutes and concentrated in vacuo. The residue was triturated in tert-butyl methyl ether (300 ml) and filtrated over a pad of Decalite. The filtrate was concentrated in vacuo. The residue was partitioned between ethyl acetate (300 ml) and 1 M aqueous sodium hydroxide solution (100 ml). The layers were separated. The organic layer was washed with one 100 ml-portion of water. The combined aqueous layers were extracted with one 150-ml portion of ethyl acetate. The combined organic layers were washed with one 50 ml-portion of brine, dried over anhydrous sodium sulfate and concentrated in vacuo to give the title compound (8.75 g, 94.6%) as colorless oil, which can be used without further purification. MS m/e: 172 (M$^+$)

Intermediates of Formula (XVII)

trans-4-Formyl-cyclohexanecarboxylic acid methyl ester

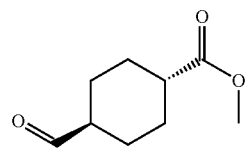

To a solution of dimethylsulfoxide (9.53 g, 122 mmol) in dry dichloromethane (400 ml) was slowly added oxalyl chloride (7.74 g, 61.0 mmol) at −78° C. The cooling bath was removed and the reaction mixture was stirred at −50° C. for 5 min. A solution of trans-4-hydroxymethyl-cyclohexanecarboxylic acid methyl ester (8.75 g, 50.8 mmol) in dichloromethane (108 ml) was added at −65° C. Stirring for 30 minutes was followed by addition of triethylamine (25.7 g, 254 mmol). The cooling bath was removed 15 minutes after completed addition. The reaction mixture was quenched with 1 M aqueous hydrochloric acid solution (152 ml, 152 mmol) at −10° C. The layers were separated. The organic layer was washed with two 250 ml-portions of water and one 100-ml portion of brine, dried over anhydrous sodium sulfate and concentrated in vacuo to give the title compound as yellow oil (9.3 g, quantitative), which was used in the next step without further purification. MS m/e: 170 (M$^+$)

Intermediates of Formula (XVIII)

trans-(E/Z)-4-(Hydroxyimino-methyl)-cyclohexanecarboxylic acid methyl ester

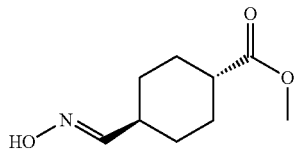

To a solution of trans-4-formyl-cyclohexanecarboxylic acid methyl ester (8.65 g, 50.8 mmol) in methanol (250 ml) was added sodium acetate (12.5 g, 152 mmol) and subsequently hydroxylamine hydrochloride (10.6 g, 152 mmol) at 0-5° C. The cooling bath was removed 10 minutes after completed addition, and the mixture was stirred for 20 h. The reaction mixture was concentrated in vacuo. The residue was partitioned between ethyl acetate (300 ml) and of 0.5 M aqueous sodium hydroxide solution. The layers were separated. The organic layer was washed with one 150-ml portion of 0.5 M aqueous sodium hydroxide solution. The combined aqueous layers were extracted with one 150 ml-portion of ethyl acetate. The combined organic layers were washed with one 150 ml-portion of 0.5 M aqueous hydrochloric acid solution and one 100-ml portion of brine, dried over anhydrous sodium sulfate and concentrated in vacuo to give the title compound (8.5 g, 90%) as colorless oil, which was used in the next step without further purification. MS m/e: 185 (M$^+$)

Intermediates of Formula (XIX)

trans-Methyl 4-(chloro(hydroxyimino)methyl)cyclohexanecarboxylate

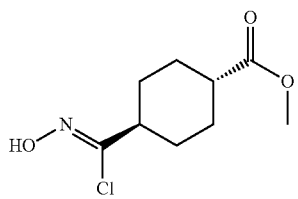

To a solution of trans-(E/Z)-4-(hydroxyimino-methyl)-cyclohexanecarboxylic acid methyl ester (5.0 g, 27 mmol) in N,N-dimethylformamide (135 ml) was added N-chlorosuccinimide (3.78 g, 28.3 mmol) at 0-5° C. The cooling bath was removed, and the mixture was stirred for 1 h. The reaction mixture was partitioned between diethyl ether (250 ml) and an ice-water mixture (200 ml). The organic layer was washed with two 200 ml-portions of water and one 100 ml-portion of brine. The combined aqueous layers were extracted with one 150-ml portion of diethyl ether. The combined organic layers were dried over anhydrous sodium sulfate and concentrated in vacuo to give the title compound (6.1 g, quantitative) as colorless viscous oil, which was used in the next step without further purification.

Intermediates of Formula (XX)

trans-4-[2-(Dimethyl-hydrazono)-cyclohexanecarbonyl]-cyclohexanecarboxylic acid methyl ester a) N'-Cyclohexylidene-N,N-dimethyl-hydrazine

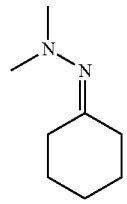

To solution of cyclohexanone (2.00 g, 20.4 mmol) and N,N-dimethylhydrazine (1.50 ml, 20.4 mmol) in ethanol (20 ml) was added a catalytic amount of toluene-4-sulfonic acid monohydrate. The reaction mixture was stirred at 70° C. for 72 h. The solvent was evaporated, and the residue was purified by Kugelrohr distillation (60-80° C., 5 mbar) to give the title compound (2.50 g, 87%) as colorless oil. MS m/e: 141 ([M+H]$^+$)

b) trans-(RS)-4-[2-(Dimethyl-hydrazono)-cyclohexanecarbonyl]-cyclohexanecarboxylic acid methyl ester

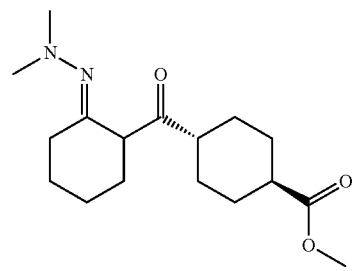

To a solution of N,N-diisopropylamine (1.59 ml, 11.2 mmol) in dry tetrahydrofuran (10 ml) was added 1.6 M n-butyl lithium in n-hexane (7.00 ml, 11.2 mmol) at 0-5° C. Addition of N'-cyclohexylidene-N,N-dimethyl-hydrazine (1.50 g, 10.7 mmol) after 15 minutes was followed by stirring for 90 minutes. The resulting solution was cannulated dropwise to a solution of trans-4-chlorocarbonyl-cyclohexanecarboxylic acid methyl ester (2.19 g, 10.7 mmol) in dry tetrahydrofuran (50 ml) at −65° C. The reaction mixture was stirred for 20 h at −78° C. The cooling bath was removed and the reaction mixture was quenched by addition of acetic acid (0.65 ml, 11 mmol) at −5° C. The mixture was partitioned between ethyl acetate (150 ml) and saturated ammonium chloride solution (100 ml). The layers were separated. The aqueous layer was extracted with one 100-ml portion of ethyl acetate. The combined organic layers were washed with one 50-ml portion of brine, dried anhydrous sodium sulfate and concentrated in vacuo. Purification with n-heptane/ethyl acetate as eluent gave the title compound (0.98 g, 30%) as light yellow oil with a purity of 60%. MS m/e: 309 ([M+H]$^+$)

4-Alkylcarbonyl-cyclohexanecarboxylic acid ester intermediates of formula (XXI)

trans-4-Cyclopentanecarbonyl-cyclohexanecarboxylic acid methyl ester

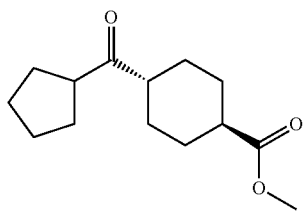 [SMILES: COC(=O)[C@H]1CC[C@H](C(=O)C2CCCC2)CC1]

To a solution of cyclopentylmegnesium chloride (2 M in diethyl ether, 6.4 ml, 12.9 mmol) in tetrahydrofurane (30 ml) was added a solution of zinc chloride (2.9 g, 21.5 mmol), which was previously dried by melting in vacuo followed by cooling under argon, in dry tetrahydrofuran (20 ml). The mixture was stirred for 45 minutes at room temperature. Addition of tetrakis(triphenylphosphine)palladium (0.25 g, 2 mol %) and subsequently trans-4-chlorocarbonyl-cyclohexanecarboxylic acid methyl ester (2.20 g, 10.7 mmol). The reaction mixture was heated at reflux for 1 h. The mixture was diluted with tert-butyl methyl ether (200 ml) and washed with one 50-ml portion of aqueous saturated ammonium chloride solution and one 30-ml portion of aqueous 1 M sodium hydroxide solution. The organic layer was dried over anhydrous sodium sulfate and concentrated in vacuo. Purification by flash-chromatography with n-heptane/ethyl acetate as eluent gave the title compound (2.36 g, 92%) as white solid. MS m/e: 239 ([M+H]$^+$)

4-Substituted Cyclohexanecarboxylic Acid Ester Intermediates of Formula (VIII)

General Procedure (V): Palladium on Charcoal Catalyzed Hydrogenation

A solution of a 4-heteroaryl-cyclohex-3-enecarboxylic acid ester intermediate of formula V and optionally an base such as triethylamine (1 eq) in an organic solvent such as ethyl acetate or toluene (0.1 M) is purged with argon. Addition of 10% palladium on activated charcoal (0.05 eq) is followed by filling the flask with hydrogen. The reaction mixture is stirred at room temperature under an atmosphere of hydrogen (1 bar) for 20-72 h. The catalyst is removed by filtration over Decalite®. The filtrate is washed with one portion of water. The aqueous layer is extracted with one or two portions of ethyl acetate. The combined organic layers are dried over anhydrous sodium sulfate and concentrated to dryness to give a cis/trans mixture of a crude 4-heteroaryl-cyclohexanecarboxylic acid ester intermediate of formula VIII, which can usually be used in the next step without further purification.

General Procedure (VI): Epimerization

A mixture of cis/trans-4-heteroaryl-cyclohexanecarboxylic acid ester intermediate of formula VIII and sodium ethylate (3-6 eq) in ethanol is heated at reflux for 20-72 h. Under these reaction conditions partial saponification of the resulting trans-4-heteroaryl-cyclohexanecarboxylic acid ester intermediate of formula VIII-b to a trans-4-heteroaryl-cyclohexanecarboxylic acid intermediate of formula IX-b may occur. Such a trans-4-heteroaryl-cyclohexanecarboxylic acid intermediate of formula IX-b can be reconverted to a trans-4-heteroaryl-cyclohexanecarboxylic acid ester intermediate of formula VIII-b by consecutive cooling of the mixture to 0-5° C., addition of concentrated sulfuric acid (7-9 eq) and heating of the mixture at reflux for 1-2 h. After cooling to room temperature the reaction mixture is partitioned between an organic solvent such as ethyl acetate or tert-butyl methyl ether and 2M aqueous sodium carbonate solution. The layers are separated. The aqueous layer is extracted with two or three portions of organic solvent. The combined organic layers are dried over anhydrous sodium sulfate and concentrated to dryness. Purification by flash-chromatography gives a trans-4-heteroaryl-cyclohexanecarboxylic acid ester intermediate of formula VIII-b.

General Procedure (VII): Arylisoxazole Formation

To a solution of an oxime intermediate of formula XV (1 eq) in tetrahydrofuran (0.1-0.2 M) is added potassium tert-butoxide (1.3 eq) at 0° C. The cooling bath is removed 15 minutes after completed addition, and the reaction mixture is stirred for 2-24 h at room temperature. The reaction mixture is partitioned between an organic solvent such as ethyl acetate or tert-butyl methyl ether and water. The layers are separated. The aqueous layer is extracted with one or two portions of organic solvent. The combined organic layers are dried over anhydrous sodium sulfate and concentrated to dryness. Purification by flash-chromatography gives a 4-arylisoxazole-cyclohexanecarboxylic acid ester intermediate of formula (XVI).

General Procedure (VIII): Arylisothiazole Formation

To a solution of a thioether intermediate of formula (XIII) (1 eq) in dichloromethane (0.1 M) is added sulfuryl chloride (1.05 eq) at 0° C. The reaction mixture is stirred for 1 h. After evaporation of the solvent the residue is re-dissolved in tetrahydrofuran (0.1 M) followed by addition of 2M ethanolic ammonia solution (10 eq) at room temperature and stirring for 2-3 h. The reaction mixture is partitioned between an organic solvent such as ethyl acetate or tert-butyl methyl ether and saturated sodium bicarbonate solution. The layers are separated. The aqueous layer is extracted with one or two portions of organic solvent. The combined organic layers are dried over anhydrous sodium sulfate and concentrated to dryness. Purification by flash-chromatography gives 4-arylisothiazole-cyclohexanecarboxylic acid ester intermediate of formula (XIV).

cis/trans-4-(3-Fluoro-pyridin-2-yl)-cyclohexanecarboxylic acid ethyl ester

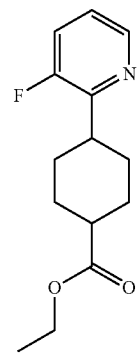

The title compound was obtained as colorless liquid in 97% yield from (RS)-4-(3-fluoro-pyridin-2-yl)-cyclohex-3-en-ecarboxylic acid ethyl ester according to general procedure (V). MS m/e: 252 ([M+H]⁺)

trans-4-(3-Fluoro-pyridin-2-yl)-cyclohexanecarboxylic acid ethyl ester

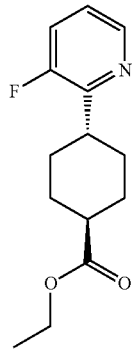

The title compound was obtained as colorless oil in quantitative yield from cis/trans-4-(3-fluoro-pyridin-2-yl)-cyclohexanecarboxylic acid ethyl ester according to general procedure (VI). MS m/e: 252 ([M−H]⁺)

trans-4-Benzo[d]isoxazol-3-yl-cyclohexanecarboxylic acid methyl ester

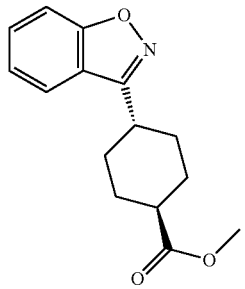 [SMILES: COC(=O)[C@H]1CC[C@H](c2noc3ccccc32)CC1]

The title compound was obtained as white solid in 71% yield from trans-4-{(2-fluoro-phenyl)-[(E/Z)-hydroxyimino]-methyl}-cyclohexanecarboxylic acid methyl ester according to general procedure (VII). MS m/e: 260 ([M+H]⁺)

trans-4-Benzo[d]isothiazol-3-yl-cyclohexanecarboxylic acid methyl ester

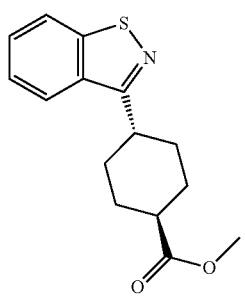 [SMILES: COC(=O)[C@H]1CC[C@H](c2nsc3ccccc32)CC1]

The title compound was obtained as white solid in 72% yield from trans-4-(2-benzylsulfanyl-benzoyl)-cyclohexanecarboxylic acid methyl ester according to general procedure (VIII). MS m/e: 276 ([M+H]+)

trans-4-(5-Methyl-isoxazol-3-yl)-cyclohexanecarboxylic acid methyl ester

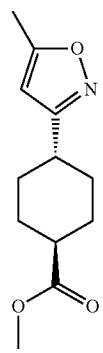 [SMILES: COC(=O)[C@H]1CC[C@H](c2cc(C)on2)CC1]

To a solution of trans-methyl 4-(chloro(hydroxyimino)methyl)cyclohexanecarboxylate (5.90 g, 26.9 mmol) and isopropenyl acetate (53.8 g, 537 mmol) in dichloromethane (134 ml) was added triethylamine (5.44 g, 53.7 mmol) at 0-5° C. The cooling bath was removed 15 minutes after completed addition, and the mixture was stirred for 20 h. The reaction mixture was concentrated in vacuo. The residue was partitioned between ethyl acetate (250 ml) and 0.1 M aqueous hydrochloric acid solution (200 ml). The organic layer was washed with one 100 ml-portion of 0.1 M aqueous hydrochloric acid solution. The combined aqueous layers were extracted with one 150 ml-portion of ethyl acetate. The combined organic layers were washed with one 200 ml-portion of 2 M sodium carbonate and one 100-ml portion of brine, dried over anhydrous sodium sulfate and concentrated in vacuo. Purification with n-heptane/ethyl acetate as eluent gave the title compound (3.00 g, 50%) as off-white solid. MS m/e: 224 ([M+H]⁺)

trans-4-(4,5,6,7-Tetrahydro-benzo[c]isoxazol-3-yl)-cyclohexanecarboxylic acid methyl ester

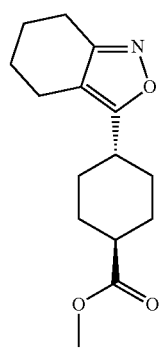 [SMILES: COC(=O)[C@H]1CC[C@H](c2onc3c2CCCC3)CC1]

A mixture of trans-4-[2-(dimethyl-hydrazono)-cyclohexanecarbonyl]-cyclohexanecarboxylic acid methyl ester (0.95 g, 3.1 mmol), sodium acetate (0.28 g, 3.4 mmol) and hydroxylamine hydrochloride (0.24 g, 3.4 mmol) in methanol (15 ml)

was stirred at room temperature for 16 h. The reaction mixture was partitioned between ethyl acetate (100 ml) and water (50 ml). The layers were separated. The aqueous layer was extracted with two 100-ml portions of ethyl acetate. The combined organic layers were dried over anhydrous sodium sulfate and concentrated in vacuo. The residue (0.88 g) was dissolved in toluene (15 ml). After addition of a catalytic amount of toluene-4-sulfonic acid monohydrate the mixture was heated at reflux for 3 h. The solvent was evaporated. Purification with n-heptane/ethyl acetate as eluent gave the title compound (0.58 g, 72%) with a regioisomeric purity of approx. 90% according to $^{13}$C-NMR. MS m/e: 264 ([M+H]$^+$)

trans-4-(5-Methyl-[1,2,4]oxadiazol-3-yl)-cyclohexanecarboxylic acid methyl ester

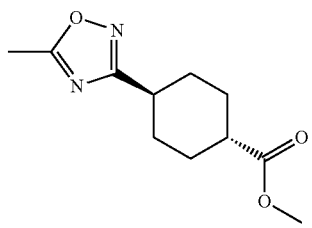

To a suspension of trans-methyl 4-(chloro(hydroxyimino) methyl)cyclohexanecarboxylate (2.46 g, 11.2 mmol) and ethyl acetamidate hydrochloride (2.77 g, 22.4 mmol) in dichloromethane (55 ml) at 0-5° C. was added triethylamine (3.10 ml, 22.4 mmol). The cooling bath was removed after 15 minutes after completed addition. After stirring over nigh the solvent was evaporated. The residue was partitioned between aqueous 1 M hydrogen chloride solution (50 ml) and ethyl acetate (50 me. The aqueous layer was extracted with two 50-ml portions of ethyl acetate. The combined organic layers were dried over anhydrous sodium sulfate and concentrated in vacuo. To a solution of the residue, a mixture of trans-4-(5-methyl-[1,2,4]oxadiazol-3-yl)-cyclohexanecarboxylic acid methyl ester and trans-(E/Z)-4-(hydroxyimino-methyl)-cyclohexanecarboxylic acid methyl ester) in N,N-dimethylformamide (33 ml) at 0-5° C. was added of N-chlorosuccinimide (1.59 g, 11.9 mmol). The cooling bath was removed and the mixture was stirred for 2 h at room temperature. The reaction mixture was partitioned between tort-butyl methyl ether (150 ml) and water (50 ml). The aqueous layer was separated. The organic layer was washed with two 50-ml portions of water and one 30-ml portion of brine, dried over anhydrous sodium sulfate and concentrated in vacuo to give a mixture of trans-methyl 4-(chloro(hydroxyimino)methyl)cyclohexanecarboxylate and trans-4-(5-methyl-[1,2,4]oxadiazol-3-yl)-cyclohexanecarboxylic acid methyl ester.

To a suspension of the mixture thus obtained and ethyl acetamidate hydrochloride (2.77 g, 22.4 mmol) in dichloromethane (55 ml) at 0-5° C. was added triethylamine (3.10 ml, 22.4 mmol). The cooling bath was removed after 15 minutes, and the reaction mixture was stirred overnight. The solvent was evaporated. The residue was partitioned between aqueous 1 M hydrogen chloride solution (50 ml) and ethyl acetate (50 ml). The aqueous layer was extracted with two 50-ml portions of ethyl acetate. The combined organic layers were dried over anhydrous sodium sulfate and concentrated in vacuo. Flash-chromatography over silica gel with n-heptane/ethyl acetate gave the title compound (1.56 g, 59%) as colorless amorphous solid. MS m/e: 225 ([M+H]$^+$)

trans-4-(Cyclopentyl-difluoro-methyl)-cyclohexanecarboxylic acid methyl ester

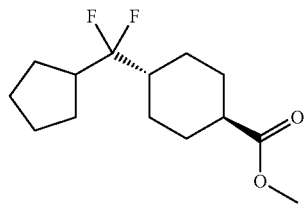 [SMILES: COC(=O)[C@H]1CC[C@H](C(F)(F)C2CCCC2)CC1]

A solution of trans-4-cyclopentanecarbonyl-cyclohexanecarboxylic acid methyl ester (1.0 g, 4.2 mmol) and DAST (1.1 ml, 8.4 mmol) in dry toluene (2 ml) was stirred at 80° C. overnight (16 h). The reaction mixture was partitioned between aqueous saturated sodium hydrogen carbonate solution (50 ml) and tert-butyl methyl ether (100 ml). The layers were separated. The aqueous layer was extracted with two 100-ml portions of tert-butyl methyl ether. The combined organic layers were dried over anhydrous sodium sulfate and concentrated in vacuo. Purification by flash-chromatography with n-heptane/ethyl acetate as eluent gave the title compound (0.13 g, 12%) as brown oil. MS m/e: 261 (M$^+$)

4-Substituted Cyclohexanecarboxylic Acid Intermediates of Formula IX trans-4-Benzo[d]isoxazol-3-yl-cyclohexanecarboxylic acid

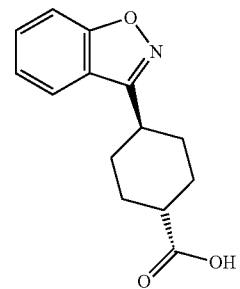

A mixture of trans-4-benzo[d]isoxazol-3-yl-cyclohexanecarboxylic acid methyl ester (6.77 g, 26.1 mmol) and aqueous 2 M sodium hydroxide solution (131 ml, 261 mmol) in 1,4-dioxane (261 ml) was stirred at room temperature for 20 h. The reaction mixture was cooled by addition of crushed ice (120 g) and acidified with concentrated hydrochloric acid (21.8 ml, 261 mmol). The reaction mixture was extracted with three 150-ml portions of ethyl acetate. The combined organic layers were washed with one 50-ml portion of brine, dried over anhydrous sodium sulfate and concentrated in vacuo.

The crude acid was crystallized from hot ethyl acetate to give the title compound (4.09 g, 64%) as white crystals. MS m/e: 246 ([M+14]+).

cis/trans-4-Isobutyl-cyclohexanecarboxylic acid (15:85)

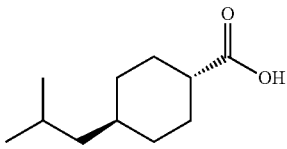

a) cis/trans-4-Isobutyl-cyclohexanecarboxylic acid (7:3)

A solution of 4-isobutylbenzoic acid (1.0 g, 5.6 mmol) in acetic acid (56 ml) was purged with argon. After addition of platinum(IV) oxide (0.38 g, 1.7 mmol) the reaction flask was filled with hydrogen gas. The reaction mixture was stirred under an atmosphere of hydrogen gas for 72 h at RT. The flask was purged with argon, and the catalyst was removed by filtration over Decalite. The filtrate was concentrated to dryness to give the title compound as a (7:3) cis/trans mixture. MS m/e: 183 ([M–H]⁻)

b) cis/trans-4-Isobutyl-cyclohexanecarboxylic acid methyl ester (7:3)

To a solution of cis/trans-4-isobutyl-cyclohexanecarboxylic acid (7:3) (1.0 g, 5.4 mmol) in methanol (54 ml) was added a catalytic amount of sulfuric acid (2 drops). The reaction mixture was heated at reflux for 16 h. The solvent was evaporated. The residue was diluted with tert-butyl methyl ether (100 ml) and washed with aqueous saturated sodium hydrogen carbonate solution (50 ml). The organic layer was dried over anhydrous sodium sulfate and concentrated to dryness to give the title compound ((7:3) cis/trans mixture) as a light yellow oil. MS m/e: 198 (M⁺)

c) cis/trans-4-Isobutyl-cyclohexanecarboxylic acid (15:85)

A 2-necked round bottom flask, which had been dried and cooled under argon, was charged with cis/trans-4-isobutyl-cyclohexanecarboxylic acid methyl ester (7:3) (0.5 g, 2.5 mmol), dry toluene (10 ml) and sodium methoxide (0.41 g, 7.6 mmol). The reaction mixture was heated at reflux for 96 h. After cooling to room temperature the mixture was diluted with tert-butyl methyl ether (100 ml) and washed with ice-cold aqueous hydrochloric acid solution (pH 1). The aqueous layer was extracted with one 50-ml portion of tert-butyl methyl ether. The combined organic layers were dried over anhydrous sodium sulfate and concentrated in vacuo to give the title compound as a (15:85) cis/trans mixture. MS m/e: 183 ([M–H]⁻)

Hydrazide Intermediates of Formula (II)

General Procedure (IX): Hydrazide Formation from Acid

To a solution of a 4-heteroaryl-cyclohexanecarboxylic acid intermediate of formula (IX) (1 eq) and triethylamine (1.05 eq) in tetrahydrofuran (0.2 M) is added ethyl chloroformate (1.05 eq) at 0° C. The reaction mixture is stirred at 0° C. for 1 h. The ammonium salts are removed by filtration. The filtrate is added to a cold solution of hydrazine hydrate (2 eq) in methanol (0.2 M). The reaction mixture is stirred at room temperature for 2-16 h. The solvent is evaporated under reduced pressure, and the residue is partitioned between an organic solvent such as ethyl acetate or dichloromethane and water. The organic layer is separated. The aqueous layer is extracted with two or three portions of organic solvent. The combined organic layers are dried over anhydrous sodium sulfate and concentrated in vacuo to give a hydrazide intermediate of formula (II), which is usually used in the next step without further purification.

General Procedure (X): Hydrazide Formation from Ester

A mixture of a 4-heteroaryl-cyclohexanecarboxylic acid ester intermediate of formula (VIII) (1 eq) and hydrazine hydrate (2-6 eq) in n-butanol (0.2-1 M) is heated at reflux for 16-72 h. After cooling to room temperature the reaction mixture is partitioned between an organic solvent such as ethyl acetate or dichloromethane and water. The layers are separated and the aqueous layer is extracted with two portions of organic solvent. The combined organic layers are dried over anhydrous sodium sulfate and concentrated in vacuo to give a hydrazide intermediate of formula (II), which is usually used in the next step without further purification.

Hydrazide 1 trans-4-(3-Fluoro-pyridin-2-yl)-cyclohexanecarboxylic acid hydrazide

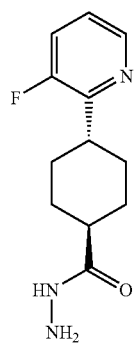

The title compound was obtained as white solid in quantitative yield from trans-4-(3-fluoro-pyridin-2-yl)-cyclohexanecarboxylic acid ethyl ester according to general procedure (X). MS m/e: 238 ([M+H]⁺)

Hydrazide 2 trans-4-Benzo[d]isoxazol-3-yl-cyclohexanecarboxylic acid hydrazide

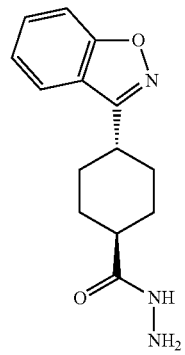 [SMILES: NNC(=O)[C@H]1CC[C@H](c2noc3ccccc32)CC1]

The title compound was obtained as white solid in 78% yield from trans-4-benzo[d]isoxazol-3-yl-cyclohexanecarboxylic acid according to general procedure (IX). MS m/e: 260 ([M+H]+)

Hydrazide 3 trans-4-Benzo[d]isothiazol-3-yl-cyclohexanecarboxylic acid hydrazide

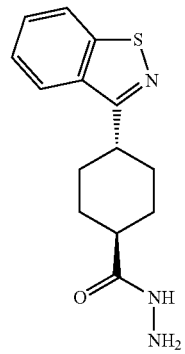 [SMILES: NNC(=O)[C@H]1CC[C@H](c2nsc3ccccc32)CC1]

The title compound was obtained as white solid in 62% yield from trans-4-benzo[d]isothiazol-3-yl-cyclohexanecarboxylic acid methyl ester according to general procedure (X). MS m/e: 275

Hydrazide 4 trans-4-(5-Methyl-isoxazol-3-yl)-cyclohexanecarboxylic acid hydrazide

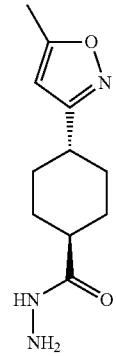

The title compound was obtained as white solid in 91% yield from trans-4-(5-methyl-isoxazol-3-yl)-cyclohexanecarboxylic acid methyl ester according to general procedure (X). MS m/e: 224 ([M+H]$^+$)

Hydrazide 5 trans-4-(5-Methyl-[1,2,4]oxadiazol-3-yl)-cyclohexanecarboxylic acid hydrazide

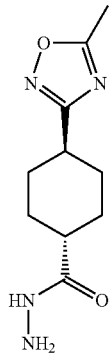

The title compound was obtained as white solid in 60% yield from trans-4-(5-methyl-[1,2,4]oxadiazol-3-yl)-cyclohexanecarboxylic acid methyl ester according to general procedure (X). MS m/e: 225 ([M+H]$^+$)

Hydrazide 6 trans-4-(4,5,6,7-Tetrahydro-benzo[c]isoxazol-3-yl)-cyclohexanecarboxylic acid hydrazide

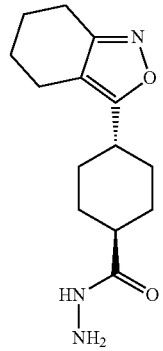 [SMILES: NNC(=O)[C@H]1CC[C@H](c2onc3c2CCCC3)CC1]

and

Hydrazide 7 trans-4-(4,5,6,7-Tetrahydro-1H-indazol-3-yl)cyclohexanecarbohydrazide

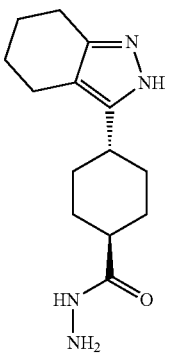 [SMILES: NNC(=O)[C@H]1CC[C@H](c2[nH]nc3c2CCCC3)CC1]

trans-4-(4,5,6,7-Tetrahydro-benzo[c]isoxazol-3-yl)-cyclohexanecarboxylic acid and trans-4-(4,5,6,7-tetrahydro-1H-indazol-3-yl)cyclohexanecarbohydrazide were obtained from trans-4-(4,5,6,7-tetrahydro-benzo[c]isoxazol-3-yl)-cyclohexanecarboxylic acid methyl ester according to general procedure (X) as a mixture, which was used in the next step without purification. MS m/e: 263, 264 ([M+H]$^+$)

Hydrazide 8 trans-4-(Cyclopentyl-difluoro-methyl)-cyclohexanecarboxylic acid hydrazide

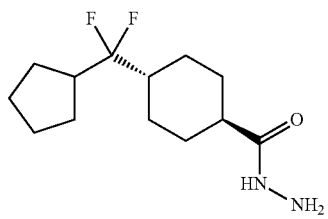 [SMILES: NNC(=O)[C@H]1CC[C@H](C(F)(F)C2CCCC2)CC1]

The title compound was obtained as light yellow solid in 88% yield from trans-4-(cyclopentyl-difluoro-methyl)-cyclohexanecarboxylic acid methyl ester according to general procedure (X). MS m/e: 261 ([M+H]$^+$)

Hydrazide 9 cis/trans-4-Isobutyl-cyclohexanecarboxylic acid hydrazide (15:85)

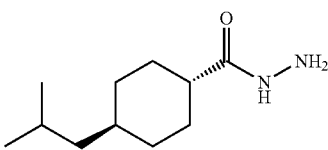

The title compound was obtained as off-white solid in 97% yield from cis/trans-4-isobutyl-cyclohexanecarboxylic acid (15:85) according to general procedure (IX). MS m/e: 199 ([M+H]+)

EXAMPLES

General Procedure (XI)

Condensation of Hydrazide and Thiolactam to Triazole

A mixture of a hydrazide derivative of formula (II) (1-1.5 eq) and a thiolactam of formula (III) (1 eq) in n-butanol (0.1-0.2 M) is heated at reflux for 16-72 h. After cooling to room temperature the solvent is evaporated and the residue is purified by flash-chromatography to give a compound of formula (I).

Example 1

8-Chloro-1-[4-(3-fluoro-pyridin-2-yl)-cyclohexyl]-4H,6H-5-oxa-2,3,10b)-triaza-benzo[e]azulene The title compound was obtained as white solid in 75% yield according to general procedure (XI).
Hydrazide: trans-4-(3-Fluoro-pyridin-2-yl)-cyclohexanecarboxylic acid hydrazide
Thiolactam: 7-Chloro-3,5-dihydrobenzo[e][1,4]oxazepine-2(1H)-thione
MS m/e: 399 ([M+H]$^+$)

Example 2

1-(4-Benzo[d]isoxazol-3-yl-cyclohexyl)-8-chloro-4H,6H-5-oxa-2,3,10b-triaza-benzo[e]azulene The title compound was obtained as off-white solid in 82% yield according to general procedure (XI).
Hydrazide: trans-4-Benzo[d]isoxazol-3-yl-cyclohexanecarboxylic acid hydrazide
Thiolactam: 7-Chloro-3,5-dihydrobenzo[e][1,4]oxazepine-2(1H)-thione
MS m/e: 421 ([M+H]$^+$)

Example 3

1-(4-Benzo[d]isothiazol-3-yl-cyclohexyl)-8-chloro-4H,6H-5-oxa-2,3,10b-triaza-benzo[e]azulene The title compound was obtained as off-white solid in 82% yield according to general procedure (XI).
Hydrazide: trans-4-Benzo[d]isothiazol-3-yl-cyclohexanecarboxylic acid hydrazide
Thiolactam: 7-Chloro-3,5-dihydrobenzo[e][1,4]oxazepine-2(1H)-thione
MS m/e: 437 ([M+H]$^+$)

Example 4

8-Chloro-1-[4-(5-methyl-isoxazol-3-yl)-cyclohexyl]-4H,6H-5-oxa-2,3,10b-triaza-benzo[e]azulene The title compound was obtained as white solid in 41% yield according to general procedure (XI).
Hydrazide: trans-4-(5-Methyl-isoxazol-3-yl)-cyclohexanecarboxylic acid hydrazide
Thiolactam: 7-Chloro-3,5-dihydrobenzo[e][1,4]oxazepine-2(1H)-thione
MS m/e: 385 ([M+H]$^+$)

Example 5

8-Chloro-1-[4-(4,5,6,7-tetrahydro-benzo[c]isoxazol-3-yl)-cyclohexyl]-4H,6H-5-oxa-2,3,10b-triaza-benzo[e]azulene Example 6

8-Chloro-1-[4-(4,5,6,7-tetrahydro-1H-indazol-3-yl)-cyclohexyl]-4H,6H-5-oxa-2,3,10b-triaza-benzo[e]azulene trans-8-Chloro-1-[4-(4,5,6,7-tetrahydro-benzo[c]isoxazol-3-yl)-cyclohexyl]-4H,6H-5-oxa-2,3,10b-triaza-benzo[e]azulene and trans-8-chloro-1-[4-(4,5,6,7-tetrahydro-1H-indazol-3-yl)-cyclohexyl]-4H,6H-5-oxa-2,3,10b-triaza-benzo[e]azulene were obtained according to general procedure (XI) after chromatographic separation.
Hydrazide: Mixture of trans-4-(4,5,6,7-tetrahydro-benzo[c]isoxazol-3-yl)-cyclohexanecarboxylic acid hydrazide and trans-4-(4,5,6,7-tetrahydro-1H-indazol-3-yl)cyclohexanecarbohydrazide Thiolactam: 7-Chloro-3,5-dihydrobenzo[e][1,4]ox-azepine-2(1H)-thione trans-8-Chloro-1-[4-(4,5,6,7-tetrahy-dro-benzo[c]isoxazol-3-yl)-cyclohexyl]-4H,6H-5-oxa-2,3,10b-triaza-benzo[e]azulene was obtained as off-white solid in 25% yield.

MS m/e: 425 ([M+H]$^+$)

trans-8-Chloro-1-[4-(4,5,6,7-tetrahydro-1H-indazol-3-yl)-cyclohexyl]-4H,6H-5-oxa-2,3,10b-triaza-benzo[e]azulene was obtained as off-white solid in 11% yield.

MS m/e: 424 ([M+H]$^+$)

Example 7

8-Chloro-1-[4-(5-methyl-[1,2,4]oxadiazol-3-yl)-cyclohexyl]-4H,6H-5-oxa-2,3,10b-triaza-benzo[e]azulene The title compound was obtained as off-white solid in 18% yield according to general procedure (XI).

Hydrazide: trans-4-(5-Methyl-[1,2,4]oxadiazol-3-yl)-cyclohexanecarboxylic acid hydrazide Thiolactam: 7-Chloro-3,5-dihydrobenzo[e][1,4]oxazepine-2(1H)-thione MS m/e: 386 ([M+H]$^+$)

Example 8

8-Chloro-1-[4-(cyclopentyl-difluoro-methyl)-cyclo-hexyl]-4H,6H-5-oxa-2,3,10b-triaza-benzo[e]azulene The title compound was obtained as off-white solid in 25% yield according to general procedure (XI).

Hydrazide: trans-4-(Cyclopentyl-difluoro-methyl)-cyclo-hexanecarboxylic acid hydrazide Thiolactam: 7-Chloro-3,5-dihydrobenzo[e][1,4]ox-azepine-2(1H)-thione MS m/e: 422 ([M+H]$^+$)

Example 9

8-Chloro-1-(4-isobutyl-cyclohexyl)-4H,6H-oxa-2,3,10b-triaza-benzo[e]azulene

The title compound was obtained as off-white solid in 42% yield according to general procedure (XI).

Hydrazide: cis/trans-4-Isobutyl-cyclohexanecarboxylic acid hydrazide (15:85)

Thiolactam: 7-Chloro-3,5-dihydrobenzo[e][1,4]ox-azepine-2(1H)-thione

MS m/e: 360 ([M+H]$^+$)

[1] Robben, et al. (2006). Am J Physiol Renal Physiol. 291, F257-70, "Cell biological aspects of the vasopressin type-2 receptor and aquaporin 2 water channel in nephrogenic diabetes insipidus"

[2] Neumann (2008). J Neuroendocrinol. 20, 858-65, "Brain oxytocin: a key regulator of emotional and social behaviours in both females and males"

[3] Ebner, et al. (2002). Eur J Neurosci. 15, 384-8, "Forced swimming triggers vasopressin release within the amygdala to modulate stress-coping strategies in rats"

[4] Kendler, et al. (2003). Arch Gen Psychiatry. 60, 789-96, "Life Event Dimensions of Loss, Humiliation, Entrapment, and Danger in the Prediction of Onsets of Major Depression and Generalized Anxiety"

[5] Regier, et al. (1998). Br J Psychiatry Suppl. 24-8, "Prevalence of anxiety disorders and their comorbidity with mood and addictive disorders"

[6] Bielsky, et al. (2004). Neuropsychopharmacology. 29, 483-93, "Profound impairment in social recognition and reduction in anxiety-like behavior in vasopressin V1a receptor knockout mice"

[7] Landgraf, et al. (1995). Regul Pept. 59, 229-39, "V1 vasopressin receptor antisense oligodeoxynucleotide into septum reduces vasopressin binding, social discrimination abilities, and anxiety-related behavior in rats"

[8] Yirmiya, et al. (2006). 11, 488-94, "Association between the arginine vasopressin 1a receptor (AVPR1a) gene and autism in a family-based study: mediation by socialization skills"

[9] Thompson, et al. (2004). Psychoneuroendocrinology. 29, 35-48, "The effects of vasopressin on human facial responses related to social communication"

[10] Raskind, et al. (1987). Biol Psychiatry. 22, 453-62, "Antipsychotic drugs and plasma vasopressin in normals and acute schizophrenic patients"

[11] Altemus, et al. (1992). Arch Gen Psychiatry. 49, 9-20, "Abnormalities in the regulation of vasopressin and corticotropin releasing factor secretion in obsessive-compulsive disorder"

[12] Michehm and Morris (1999). Ann N Y Acad Sci. 897, 198-211, "Endogenous vasopressin modulates the cardiovascular responses to exercise"

[13] Van Kerckhoven, et al. (2002). Eur J Pharmacol. 449, 135-41, "Chronic vasopressin V(1A) but not V(2) receptor antagonism prevents heart failure in chronically infarcted rats"

[14] Brouard, et al. (2000). Bjog. 107, 614-9, "Effect of SR49059, an orally active V1a vasopressin receptor antagonist, in the prevention of dysmenorrhoea"

[15] Aughton, et al. (2008). Br J Pharmacol. doi:10.1038/bjp.2008.253, "Pharmacological profiling of neuropeptides on rabbit vaginal wall and vaginal artery smooth muscle in vitro"

[16] Gupta, et al. (2008). Br J Pharmacol. 155, 118-26, "Oxytocin-induced contractions within rat and rabbit ejaculatory tissues are mediated by vasopressin V(1A) receptors and not oxytocin receptors"

[17] Goodman and Gilman's "The Pharmacological Basis of Therapeutics, 7th ed." in page 35, Macmillan Publ. Company, Canada, 1985

[18] Compendium of Chemical Terminology, 2nd, A. D. McNaught & A. Wilkinson (Eds). Blackwell Scientific Publications, Oxford (1997)

The invention claimed is:

1. A compound of formula I,

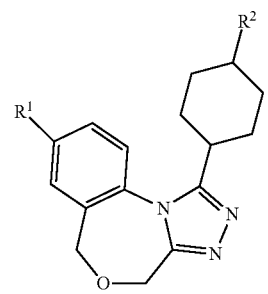

wherein
R¹ is halogen;
R² is selected from the group consisting of
  i) heteroaryl, unsubstituted or substituted by 1 to 3 substituents individually selected from the group consisting of OH, halogen, cyano, $C_{1-6}$-alkyl, $C_{1-6}$-alkoxy, halogen-$C_{1-6}$-alkyl, halogen-$C_{1-6}$-alkoxy, $C_{1-6}$-alkoxy-$C_{1-6}$-alkyl and hydroxy-$C_{1-6}$-alkyl;
  ii) aryl, unsubstituted or substituted by 1 to 3 substituents individually selected from the group consisting of OH, halogen, cyano, $C_{1-6}$-alkyl, $C_{1-6}$-alkoxy, halogen-$C_{1-6}$-alkyl, halogen-$C_{1-6}$-alkoxy, $C_{1-6}$-alkoxy-$C_{1-6}$-alkyl and hydroxy-$C_{1-6}$-alkyl;
  iii) $C_{3-7}$-cycloalkyl, unsubstituted or substituted by 1 to 3 substituents individually selected from the group consisting of OH, halogen, cyano, $C_{1-6}$-alkyl, $C_{1-6}$-alkoxy, halogen-$C_{1-6}$-alkyl, halogen-$C_{1-6}$-alkoxy, $C_{1-6}$-alkoxy-$C_{1-6}$-alkyl and hydroxy-$C_{1-6}$-alkyl; and
  iv) $C_{1-6}$-alkyl, unsubstituted or substituted by 1 to 3 substituents individually selected from the group consisting of OH, halogen, cyano, $C_{3-7}$-cycloalkyl, $C_{1-6}$-alkoxy and halogen-$C_{1-6}$-alkoxy;
or pharmaceutically acceptable salts thereof.

2. A compound according to claim 1, wherein R¹ is chloro.

3. A compound of claim 1, wherein R² is selected from the group consisting of unsubstituted heteroaryl, heteroaryl substituted by halogen or $C_{1-6}$-alkyl, unsubstituted $C_{1-6}$-alkyl and $C_{1-6}$-alkyl substituted by halogen and $C_{3-7}$-cycloalkyl.

4. A compound of claim 1, wherein R² is selected from the group consisting of 3-fluoro-pyridinyl, 4-benzo[d]isothiazolyl, 5-methyl-[1,2,4]oxadiazolyl, 5-methyl-isoxazolyl, 4,5,6,7-tetrahydro-benzo[c]isoxazolyl, 4, 5, 6,7-tetrahydro-1H-indazolyl, isobutyl, cyclopentyl-difluoro-methyl and 4-benzo[d]isoxazolyl.

5. A compound of claim 1, selected from the group consisting of
  8-Chloro-1-[4-(3-fluoro-pyridin-2-yl)-cyclohexyl]-4H,6H-5-oxa-2,3,10b-triaza-benzo[e]azulene,
  1-(4-Benzo[d]isothiazol-3-yl-cyclohexyl)-8-chloro-4H,6H-5-oxa-2,3,10b-triaza-benzo[e]azulene,
  8-Chloro-1-[4-(5-methyl-[1,2,4]oxadiazol-3-yl)-cyclohexyl]-4H,6H-5-oxa-2,3,10b-triaza-benzo[e]azulene,
  8-Chloro-1-[4-(5-methyl-isoxazol-3-yl)-cyclohexyl]-4H,6H-5-oxa-2,3,10b-triaza-benzo[e]azulene,
  8-Chloro-1-[4-(4,5,6,7-tetrahydro-benzo[c]isoxazol-3-yl)-cyclohexyl]-4H,6H-5-oxa-2,3,10b-triaza-benzo[e]azulene,
  8-Chloro-1-[4-(4,5,6,7-tetrahydro-1H-indazol-3-yl)-cyclohexyl]-4H,6H-5-oxa-2,3,10b-triaza-benzo[e]azulene,
  8-Chloro-1-(4-isobutyl-cyclohexyl)-4H,6H-5-oxa-2,3,10b-triaza-benzo[e]azulene,
  8-Chloro-1-[4-(cyclopentyl-difluoro-methyl)-cyclohexyl]-4H,6H-5-oxa-2,3,10b-triaza-benzo[e]azulene, and
  1-(4-Benzo[d]isoxazol-3-yl-cyclohexyl)-8-chloro-4H,6H-5-oxa-2,3,10b-triaza-benzo[e]azulene,
or pharmaceutically acceptable salts thereof.

6. A process for preparing a compound of claim 1, which process comprises reacting a compound of formula II with a compound of formula III to a compound of formula I

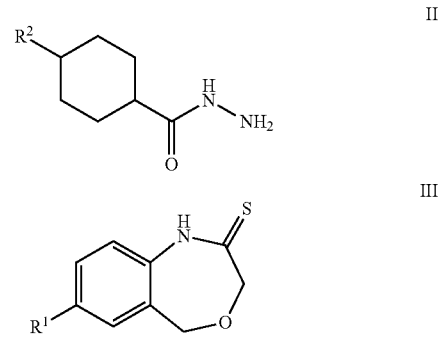

wherein R¹ and R² are as defined in claim 1.

7. A compound prepared by a process as defined in claim 6.

8. A pharmaceutical composition comprising a compound of claim 1 and a pharmaceutically acceptable carrier and/or a pharmaceutically acceptable auxiliary substance.

* * * * *